(12) United States Patent
Siyan et al.

(10) Patent No.: US 8,269,023 B2
(45) Date of Patent: Sep. 18, 2012

(54) PROCESS FOR PREPARATION OF DULOXETINE HYDROCHLORIDE

(75) Inventors: Rajinder Singh Siyan, Pune (IN); Sunil Kumar Vinubhai Gohel, Pune (IN); Girij Pal Singh, Pune (IN)

(73) Assignee: Lupin Ltd., Mumbai (IN)

( * ) Notice: Subject to any disclaimer, the term of this patent is extended or adjusted under 35 U.S.C. 154(b) by 339 days.

(21) Appl. No.: 12/530,214

(22) PCT Filed: Mar. 5, 2008

(86) PCT No.: PCT/IN2008/000125
§ 371 (c)(1),
(2), (4) Date: Oct. 14, 2009

(87) PCT Pub. No.: WO2008/107911
PCT Pub. Date: Sep. 12, 2008

(65) Prior Publication Data
US 2010/0105925 A1    Apr. 29, 2010

(30) Foreign Application Priority Data

| Mar. 5, 2007 | (IN) | ............................. 312/KOL/2007 |
| Aug. 27, 2007 | (IN) | ........................... 1172/KOL/2007 |
| Aug. 27, 2007 | (IN) | ........................... 1343/KOL/2007 |

(51) Int. Cl.
*C07D 333/16* (2006.01)
(52) U.S. Cl. ........................................... 549/65
(58) Field of Classification Search ............ 549/65
See application file for complete search history.

(56) References Cited

U.S. PATENT DOCUMENTS

| 4,956,388 A | 9/1990 | Robertson et al. |
| 5,023,269 A | 6/1991 | Robertson et al. |
| 5,362,886 A | 11/1994 | Berglund |
| 6,541,668 B1 | 4/2003 | Kjell et al. |
| 2006/0270859 A1 | 11/2006 | Ini et al. |
| 2006/0270861 A1 | 11/2006 | Ini et al. |
| 2006/0276660 A1 | 12/2006 | Ini et al. |

FOREIGN PATENT DOCUMENTS

| EP | 1 820 800 | 8/2007 |
| WO | 2004/056795 | 7/2004 |
| WO | 2006/027798 | 3/2006 |
| WO | 2006/045255 | 5/2006 |
| WO | 2006/099433 | 9/2006 |
| WO | 2006/126213 | 11/2006 |
| WO | 2007/077580 | 7/2007 |

OTHER PUBLICATIONS

Patent Cooperation Treaty, "International Preliminary Report on Patentability," IB/WIPO, by Officer Mülhausen, Dorothee, in PCT Application No. PCT/IN2008100125; Document of 11 pages, dated Sep. 8, 2009.

*Primary Examiner* — Taofiq A Solola
(74) *Attorney, Agent, or Firm* — Akerman Senterfitt; Peter A. Chiabotti

(57) ABSTRACT

An improved process for synthesis of duloxetine hydrochloride (1) having chiral purity greater than 99.9% that is characterized by the following:

(i) preparation of racemic condensed compound (RS)—N,N-di methyl-3-(1-naphthyloxy)-3-(2-thienyl)propanamine (4) by reaction of racemic hydroxy compound (2) with 1-fluoronaphthalene (3) in presence of a base such as sodamide, potassium amide or potassium bis(trimethylsilyl)amide (KHDMS) in polar aprotic solvent, (ii) optical resolution of racemic condensed compound (5a+5b) with di-benzoyl-L-tartaric acid (7, DBTA, R=H) or di-para-anisoyl-L-tartaric acid (7, DATA, R=OCH$_3$) to obtain crude (S)—N.N-dimethyl-3-(1-naphthyloxy)-3-(2-thienyl)propanamine dibenzoyl tartarate salt (8a) or (S)—N.N-dimethyl-3-(1-naphthyloxy)-3-(2-thienyl)propanamine di-p-anisoyl tartarate salt (9a) respectively, (iii) optionally purification of crude tartarate salts (8a or 9a) by crystallization, (iv) optionally purification of duloxetine hydrochloride (1) by crystallization and (v) racemization of undesired (R)—N,N-di methyl-3-(1-naphthyloxy)-3-(2-thienyl)propanamine (5b) by treatment with base potassium bis(trimethylsilyl)amide (KHDMS) to obtain racemic mixture of condensed compounds (5a and 5b).

47 Claims, 4 Drawing Sheets

PROCESS FOR PREPARATION OF DULOXETINE HYDROCHLORIDE

TECHNICAL FIELD OF THE INVENTION

The present invention relates to novel process for synthesis of duloxetine hydrochloride of formula (1) in chiral purity of greater than 99.9%.

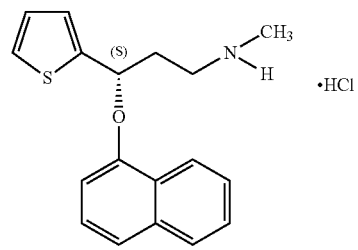

BACKGROUND OF THE INVENTION

The chemical name of duloxetine hydrochloride is (S)-(+)-N-methyl-3-(1-naphthyloxy)-3-(2-thienyl)propanamine hydrochloride (1).

Duloxetine was disclosed in U.S. Pat. No. 4,956,388 and its acid addition salts in U.S. Pat. No. 5,362,886. Duloxetine hydrochloride is useful for the treatment as an anti-depressant and also for treatment of urinary incontinence. It is the active ingredient of drug "CYMBALTA".

Very few references are directed towards chiral synthesis of chiral starting compound (S)—N.N-dimethyl-3-hydroxy-3-(2-thienyl)propanamine of formula

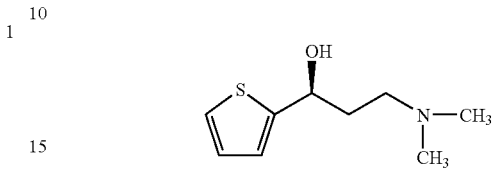

and it's use in the asymmetric synthesis of duloxetine.

Numbers of documents are cited in the patent as well as academic literature for the synthesis of duloxetine and its enantiomerically pure intermediate compounds via an optical resolution of racemic duloxetine or racemic intermediates that are formed in the synthesis of duloxetine at different steps. These pathways are illustrated in the following synthetic scheme I.

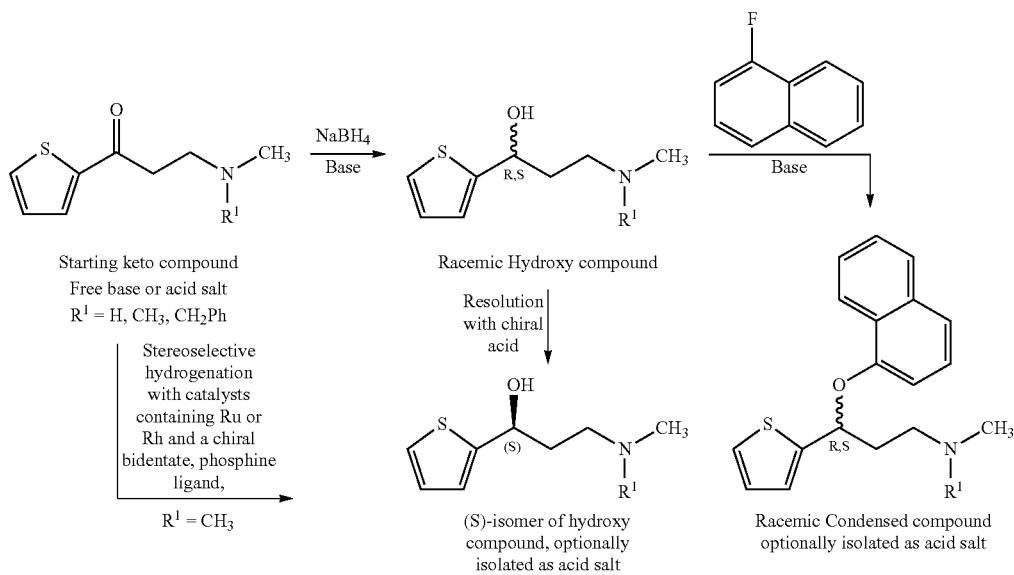

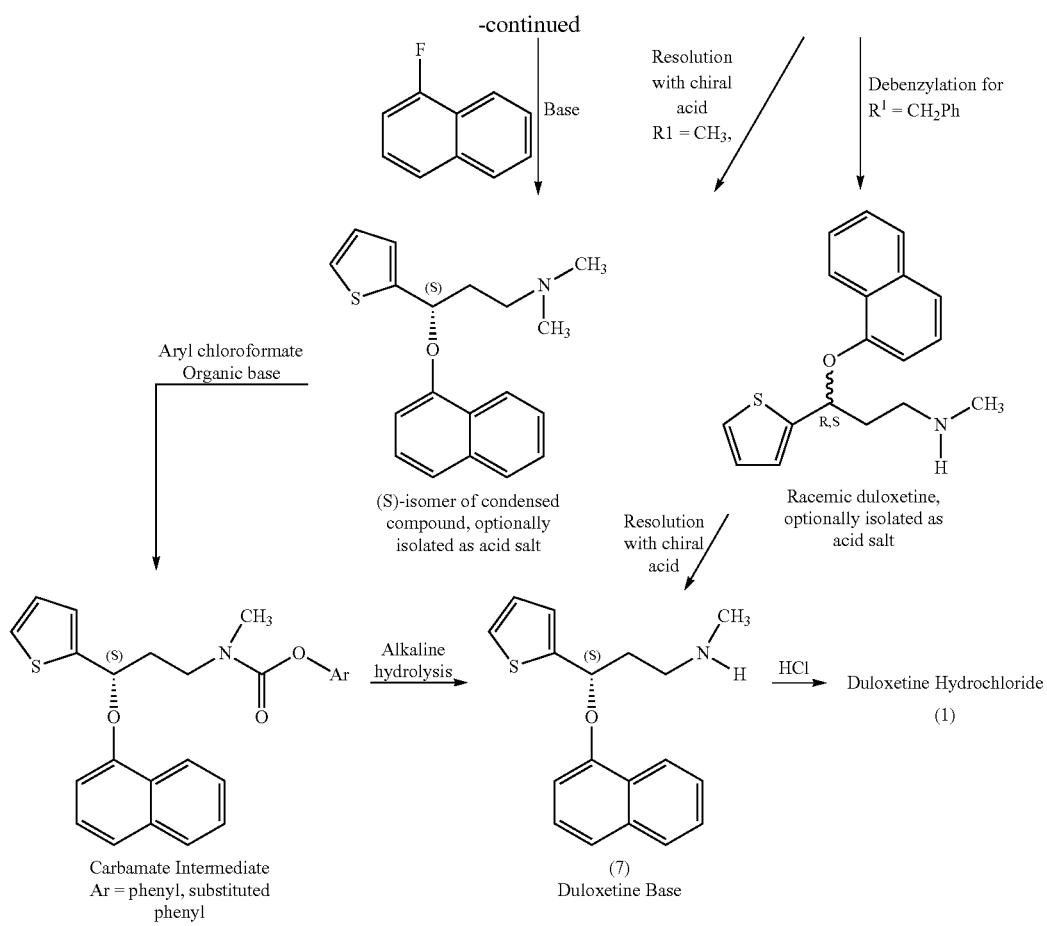

Carbamate Intermediate
Ar = phenyl, substituted phenyl (7)
Duloxetine Base

Most of the literature data indicate that the initial step of duloxetine synthesis is condensation of either racemic hydroxy compound i.e. (RS)—N.N-dimethyl-3-hydroxy-3-(2-thienyl)propanamine or enantiomerically pure (S)—N.N-dimethyl-3-hydroxy-3-(2-thienyl)propanamine with 1-fluoronaphthalene by using sodium hydride as base in polar aprotic solvent. Sodium hydride is very hazardous reagent because it is pyrophoric and reacts violently with water with evolution of hydrogen gas.

The inventors of WO 2004/056,795 have successfully replaced sodium hydride with alkali metal hydroxides, alkali metal carbonates, alkali metal bicarbonates preferably with potassium hydroxide but the condensation reaction requires to be carried out in presence of phase transfer catalyst such as crown ethers, quaternary ammonium salts, quaternary phosphonium salts to facilitate the reaction. The use of phase transfer catalysts render the process economically non viable since they are much costlier.

U.S. Pat. No. 6,541,668 describes synthesis of 3-aryloxy-3-arylpropanamines by reaction of alkoxide of 3-hydroxy-3-arylpropanamine with a halo-aromatic in 1,3-dimethyl-2-imidazolidinone or N-methylpyrrolidinone as solvent. The alkoxides are very strong bases and therefore are hazardous that brings limitation on their use on large scale.

WO 2006/126,213 describe condensation of racemic hydroxy compound with 1-fluoronaphthalene in organic polar solvent such as dimethyl sulfoxide, dimethyl formamide, dimethyl acetamide in presence of alkoxide base such as sodium methoxide, sodium ethoxide and potassium tert. butoxide. As mentioned above, the alkoxides are very strong bases and hazardous which restrict their use on plant scale reactions.

Thus, the methods described in prior art for condensation of racemic hydroxy compound with 1-fluoronaphthalene that utilizes sodium hydride, alkoxide or phase transfer catalyst for large-scale reactions suffers from several drawbacks, such as:

1) potentially hazardous reagents are used,
2) sodium hydride pyrophoric, it catches fire on contact with moisture,
3) very toxic reagents are used,
4) requires special skills to handle,
5) requires anhydrous medium for performing the reaction,
6) costlier reagent and
7) difficult to carry out plant scale reactions.

These drawbacks of the condensation reactions associated with the prior art processes are overcome by the present invention in which the condensation is achieved by using milder bases such as sodamide potassium amide and potassium bis(trimethylsilyl)amide (see scheme II).

There are several reports on optical resolution of racemic duloxetine and it's racemic intermediates by using resolving chiral acids such as tartaric acid, dibenzoyl-L-tartaric acid, di-p-toluoyl-L-tartaric acid, mandelic acid, camphor sulphonic acid, (S)-2-pyrrolidine-2-one-5-carboxylic-acid and (−)-2,3,4,6-di-O-isopropylidine-2-keto-L-gulonic acid. However, very few of them are directed towards resolution of racemic condensed compound (RS)—N.N-di methyl-3-(1-naphthyloxy)-3-(2-thienyl)propanamine (5a+5b) to obtain (S)—N,N-dimethyl-3-(1-naphthylenyloxy)-3-(2-thienyl)propanamine (5a), which is key intermediate in synthesis of duloxetine hydrochloride. Theses references are discussed below.

The example 1 of U.S. Pat. No. 5,023,269 discloses general method for preparation of (R,S)N,N-dimethyl-3-(1-naphthylenyloxy)-3-(2-thienyl)propanamine (5a+5b) that is isolated as its oxalate salt. This patent although mentions that the resolution of racemic mixture 5a+5b can be carried out using resolving agent such as dibenzoyl-D-tartaric acid and dibenzoyl-L-tartaric acid (referred to as DBTA hereafter) and the like, however, it does not provide an enabling disclosure for the same.

WO 2006/045255 teaches the use of D-tartaric acid to resolve racemic N,N-dimethyl-3-(1-naphthylenyloxy)-3-(2-thienyl)propanamine (5a+5b) followed by two recrystallizations of the resulting tartarate salt from tetrahydrofuran as solvent to preferentially isolate (S)—N,N-dimethyl-3-(1-naphthylenyloxy)-3-(2-thienyl)propanamine-(D)-tartarate salt in 25% yield and 99% chiral purity.

WO 2006/027798 teaches use of di-p-toluloyl-L-tartaric acid as a resolving agent for resolution of racemic N,N-dimethyl-3-(1-naphthylenyloxy)-3-(2-thienyl)propanamine (5a+5b) to obtain (S)—N,N-dimethyl-3-(1-naphthylenyloxy)-3-(2-thienyl)propanamine-di-p-toluoyl-(L)-tartarate salt in 34.8% yield and having chiral purity of about 98%. This PCT application further mentions about poor efficiency of dibenzoyl-L-tartaric acid and higher cost of chiral resolving agents such as (S)-2-pyrrolidine-2-one-5-carboxylic-acid and (−)-2,3,4,6-di-O-isopropylidine-2-keto-L-gulonic acid.

WO 2006/126213 teaches resolution of racemic N,N-dimethyl-3-(1-naphthylenyloxy)-3-(2-thienyl)propanamine (5a+5b) using D(−)-tartaric acid from ethyl acetate-isopropyl alcohol solvent mixture to get (S)—N,N-dimethyl-3-(1-naphthylenyloxy)-3-(2-thienyl)propanamine-(D)-tartarate salt as hemi hydrate in 22% yield.

US 2006/0270861 A1 covers a process for preparing enantiomerically enriched (S)-(+)-N.N-di methyl-3-(1-naphthyloxy)-3-(2-thienyl)propanamine (5b) by resolution of (R,S)—N.N-di methyl-3-(1-naphthyloxy)-3-(2-thienyl)propanamine (5a+5b) with an enantiomerically pure acid that include dibenzoyl-L-tartaric acid also, however, it does not provide any enabling disclosure for use of dibenzoyl-L-tartaric acid.

The inventors of the present invention have developed a novel process for optical resolution of racemic condensed compound (RS)—N.N-di methyl-3-(1-naphthyloxy)-3-(2-thienyl)propanamine (5a+5b) with di-benzoyl-L-tartaric acid (DBTA) and di-p-anisoyl-L-tartaric acid (DATA) as resolving agents.

None of the prior art references discussed above provide an enabling disclosure for use of DBTA or DATA as a resolving agent for resolution of (R,S)—N,N-dimethyl-3-(1-naphthylenyloxy)-3-(2-thienyl)propanamine (5a+5b). Further the methods reported in prior art for resolution of (R,S)—N,N-dimethyl-3-(1-naphthylenyloxy)-3-(2-thienyl)propanamine (5a+5b) either provide misleading information or have several disadvantages, as discussed below:

1. The patent application WO 2006/027798 states that chiral acids such as dibenzoyl tartaric acids, mandelic acid and camphorsulphonic acid have been found to be ineffective resolving agent,
2. The process as disclosed in the patent applications WO2006/126213 and WO2006/027798 uses ethyl acetate-isopropyl alcohol mixture and ethyl acetate respectively as solvents. The present inventors have studied efficiency of DBTA in these solvents along with other solvents. The results of this comparative study is provided in table 1 below which reveals that resolution was poor in ethyl acetate and in the mixture of ethyl acetate-IPA as solvent. In ethyl acetate as solvent, the content of R isomer in the product obtained after resolution was as high as 8.2% while with ethyl acetate-IPA mixture it was 7.0%.
3. The resolving agents like (S)-2-pyrrolidine-2-one-5-carboxylic-acid, (−)-2,3,4,6-di-O-isopropylidine-2-keto-L-gulonic acid, mandelic acid and camphorsulphonic acid that are used in prior art are very expensive, rendering the method uneconomical.
4. The resolution methods discussed in prior art gives (S)—N,N-dimethyl-3-(1-naphthylenyloxy)-3-(2-thienyl)propanamine (5b) in comparatively low chiral purity e.g. the resolution method discussed in WO2006/45255 gives 99% chiral purity while the process in WO2006/027798 gives 98% ee.

The preparation 2 of example 2 of U.S. Pat. No. 5,362,886 describes crystallization of duloxetine hydrochloride from ethyl acetate but without providing any data on the crystalline form. The later U.S. patent application 2006/0270859 state that the crystalline duloxetine hydrochloride obtained by the process described in U.S. Pat. No. 5,362,886 is anhydrous form which is referred as Form A. The patent application 2006/0270859 covers another crystalline Form B of duloxetine hydrochloride and process for its preparation that comprises of providing solution of duloxetine hydrochloride in water and a solvent selected from the group consisting of $C_{1-4}$ alcohols and removing the solvent.

Another U.S. patent application 2006/0276660 A1 describe process for purification of duloxetine hydrochloride comprising crystallization of duloxetine hydrochloride from water or a solvent selected from group consisting of $C_{3-8}$ ketones, $C_{3-8}$ esters, $C_{2-8}$ ethers, $C_{2-8}$ alcohols and mixtures thereof with water.

WO 2007/077580 A2 describe process for purification of duloxetine hydrochloride comprising crystallization of duloxetine hydrochloride from solvent or mixture of solvents selected from ester solvents like methyl acetate, ethyl acetate, ethyl formate, propyl acetate, isopropyl acetate, methyl isopropyl acetate and or alcohol solvents like methanol, ethanol, isopropyl alcohol or mixture of ester and alcohol solvents.

EP 1,820,800 A1 mentions that Form A of duloxetine hydrochloride may be crystallized out of a solution of duloxetine hydrochloride in water; alcohols, such as, methanol, ethanol, 1-propanol, 2-propanol, 1-butanol, isobutanol, tert-butanol, 2-methoxyethanol, 2,2,2-trifluoroethanol; or acetonitrile, nitromethane, 1,2-dimethoxyethane; or esters, such as methyl acetate, ethyl acetate, ethyl formate; or ketones, such as e.g. acetone, 2-butanone; or mixtures thereof, or mixtures with water.

The present invention provides a process for crystallization of duloxetine hydrochloride (1) from a solvent selected from alcohols such as methanol, ethanol, n-propanol, isopropanol; ketones such as acetone, methyl ethyl ketone; esters such as methyl acetate, ethyl acetate, ethyl formate, propyl acetate or a mixtures thereof.

In summary, the inventors of the present invention have developed a process for preparation of duloxetine hydrochloride (1) having chiral purity greater than 99.9% that not only overcome the disadvantages of processes in the prior art but also is safer, efficient, economically viable and easy to operate on plant scale. The process is discussed below in detail.

OBJECTIVE OF THE INVENTION

The objective of the present invention is to provide a method for synthesis of duloxetine hydrochloride (1) having chiral purity greater than 99.9% that is safer and easy to operate on plant scale.

SUMMARY OF THE INVENTION

The present invention provides an improved, safer and easy to operate on plant scale process for synthesis of duloxetine hydrochloride (1) having chiral purity of greater than 99.9%. The process is characterized by the following:

(i) preparation of racemic condensed compound (RS)—N,N-di methyl-3-(1-naphthyloxy)-3-(2-thienyl)propanamine (4) by reaction of racemic hydroxy compound (2) with 1-fluoronaphthalene (3) in presence of milder bases such as sodamide, potassium amide or potassium bis(trimethylsilyl)amide (KHDMS) in polar aprotic solvent, (ii) optical resolution of racemic condensed compound (5a+5b) with di-benzoyl-L-tartaric acid (7, R=H; referred as DBTA hereafter) or di-para-anisoyl-L-tartaric acid (7, R=OCH$_3$ referred as DATA hereafter) to obtain crude (S)—N.N-dimethyl-3-(1-naphthyloxy)-3-(2-thienyl)propanamine dibenzoyl tartarate salt (8a) or (S)—N.N-dimethyl-3-(1-naphthyloxy)-3-(2-thienyl)propanamine di-p-anisoyl tartarate salt (9a) respectively, (iii) optionally purification of crude tartarate salt (8a or 9a) by crystallization, (iv) optionally purification of duloxetine hydrochloride (1) by crystallization and (v) racemization of undesired (R)—N,N-di methyl-3-(1-naphthyloxy)-3-(2-thienyl)propanamine (6b) by treatment with base potassium bis(trimethylsilyl)amide (referred as KHDMS hereafter) to obtain racemic condensed compound (6a+6b).

DETAILED DESCRIPTION OF THE INVENTION

Figure 1:
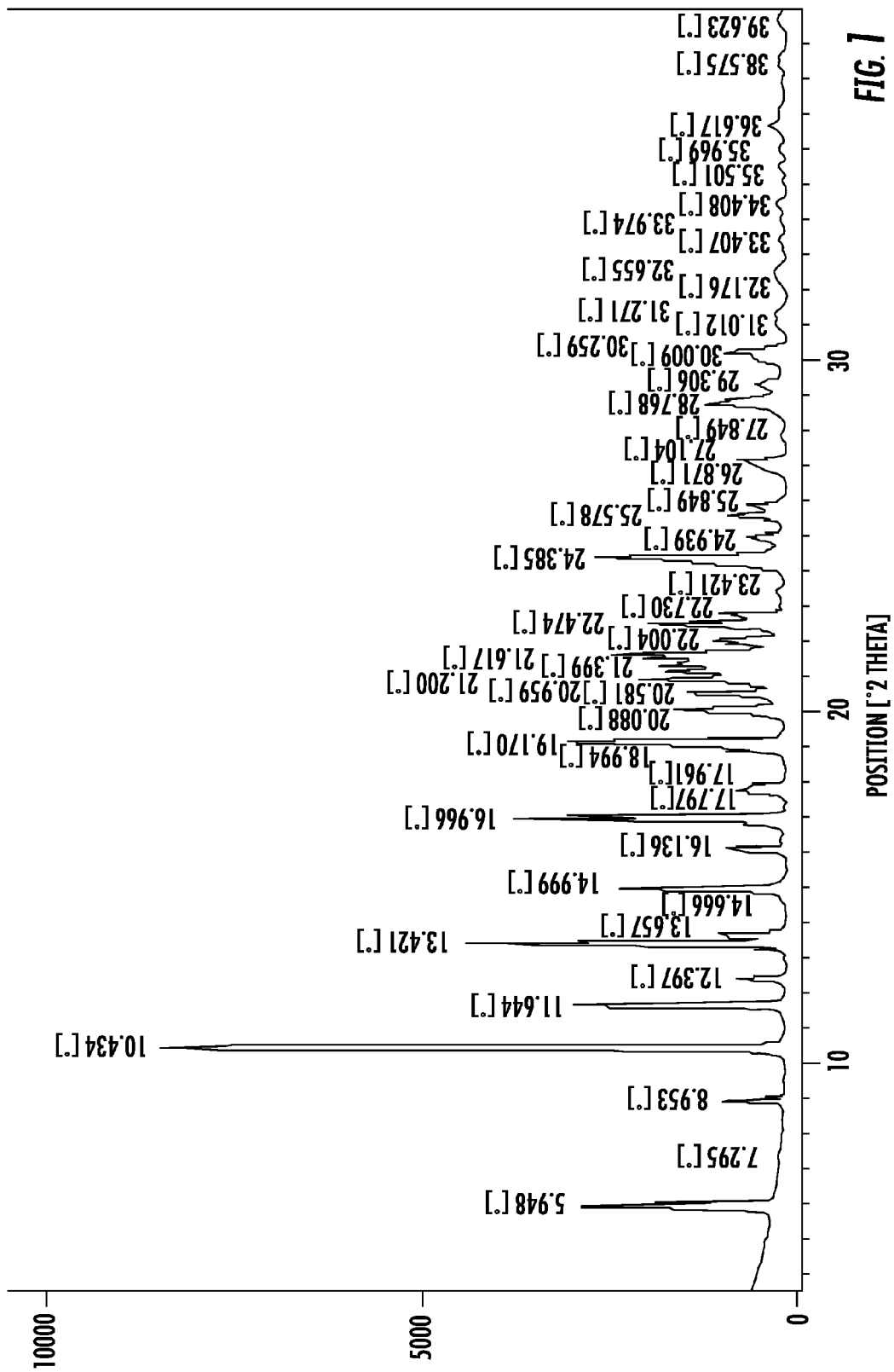
FIG. 1 Powder X-ray diffractogram of Form I of crystalline (S)—N,N-dimethyl-3-(1-napthlalenyloxy)-3-(2-thienyl) propanamine dibenzoyl L-tartarate salt (8a).

The present invention provides a novel process for synthesis of duloxetine hydrochloride (1) having chiral purity of greater than 99.9% that comprises of the following steps:

i) reaction of (RS)—N.N-di methyl-3-hydroxy-3-(2-thienyl)propanamine (2, racemic hydroxy compound) with 1-fluoronaphthalene (3) in aprotic polar organic solvent in presence of a base selected from sodamide, potassium amide, potassium bis(trimethylsilyl)amide to obtain (RS)—N.N-di methyl-3-(1-naphthyloxy)-3-(2-thienyl)propanamine (4) (racemic condensed compound), ii) optionally isolation of racemic condensed compound as acid addition salt (5) of organic or inorganic acid, iii) conversion of salt (5) to free base (RS)—N.N-di methyl-3-(1-naphthyloxy)-3-(2-thienyl)propanamine (6a+6b) by treatment with base, iv) optical resolution of free base of racemic condensed compound (6a+6b) with DBTA (7, R=H) or DATA (7, R=OCH$_3$) in organic solvent to get tartarate salt of (S)-isomer (8a or 9a), v) optionally purification of tartarate salt of (S)-isomer (8a or 9a) by crystallization from suitable organic solvent or mixture of two or more solvents, vi) conversion of tartarate salt (8a or 9a) to free base (S)—N.N-di methyl-3-(1-naphthyloxy)-3-(2-thienyl)propanamine (5a) by treatment with base, vii) demethylation of free base (6a) by treatment with phenyl chloroformate in presence of diisopropylethyl amine in toluene to get carbamate intermediate (10) in situ, viii) hydrolysis of carbamate intermediate (10) with sodium hydroxide in dimethyl sulfoxide solvent to give duloxetine base (11), ix) conversion of duloxetine base (11) to duloxetine hydrochloride (1) in an organic solvent or mixture of organic solvents, and x) optionally purification of duloxetine hydrochloride (1) by crystallization.

The steps involved in the synthesis of duloxetine hydrochloride (1) according to the process of present invention are depicted in synthetic scheme II given below.

Scheme II

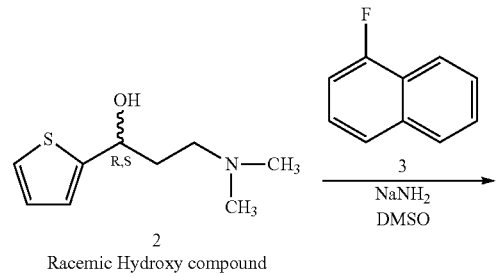

Racemic Hydroxy compound

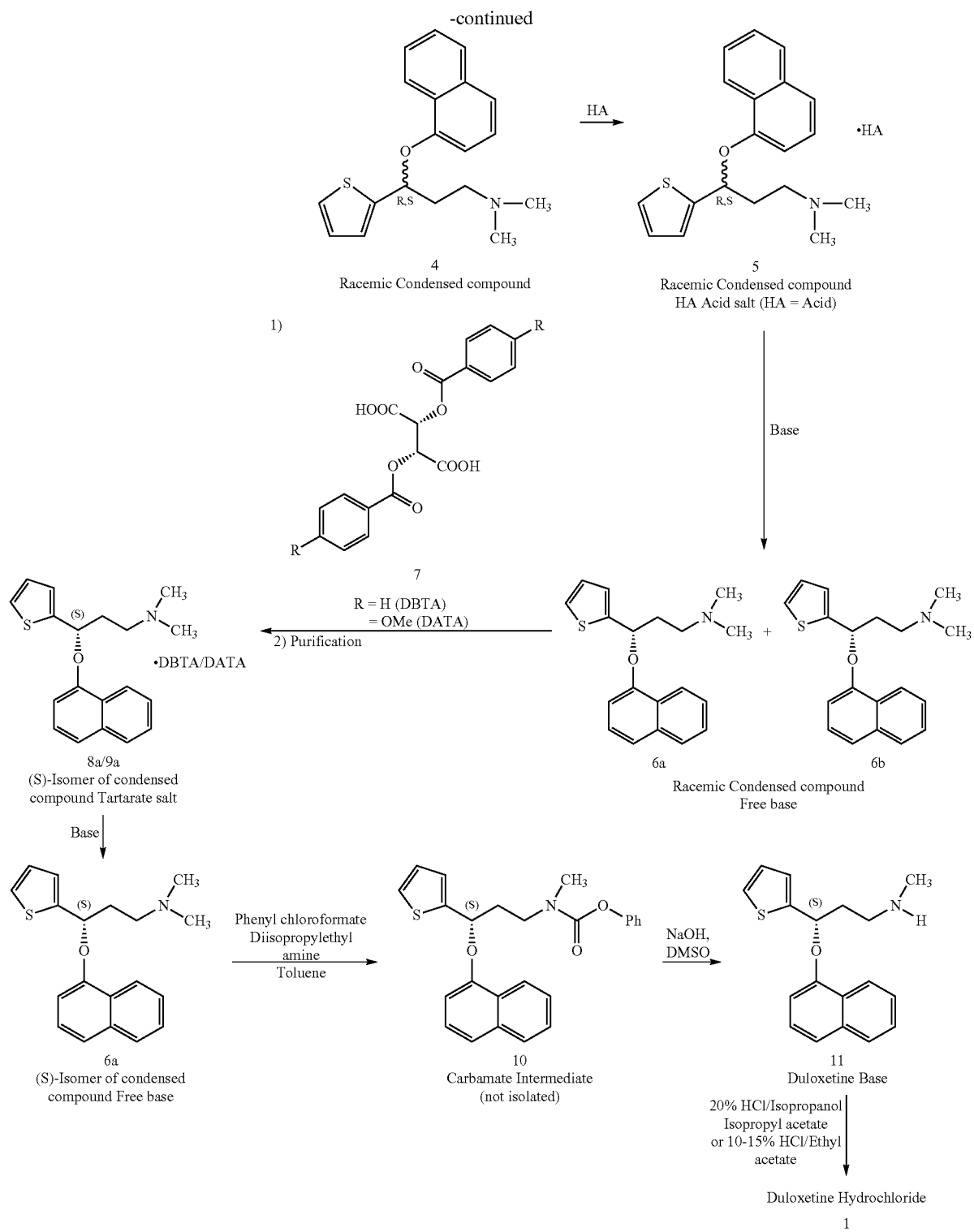

In one aspect, the present invention provides a safer and convenient method for condensation reaction of (±)-N,N-dimethyl-3-(2-thienyl)-3-hydroxypropanamine (2) (racemic hydroxy compound) with 1-fluoronaphthalene (3) to obtain (±)-N,N-dimethyl-3-(2-thienyl)-3-(1-naphthalenyloxy)propanamine (4) (racemic condensed compound). The reaction is carried out in presence of base selected from sodamide, potassium amide and potassium bis(trimethylsilyl)amide; the most preferred base is sodamide. The reaction is carried out with molar ratio of racemic hydroxy compound to base in the range from 1:1 to 1:5, preferably 1:1.5. The reaction is carried out in aprotic polar solvent selected from dimethyl sulfoxide, sulfolane, dimethyl formamide, dimethyl acetamide, N-methylpyrrolidine-2-one, preferably in dimethyl sulfoxide. The temperature of reaction at which it is carried out varies from room temperature to 150° C., preferably at 70-100° C., most preferably at 80-90° C. The racemic condensed compound (4) prepared according to the present invention as described above can be isolated as acid addition salt (5) of organic or inorganic acid such as hydrochloric acid, sulfuric acid, phosphoric acid, methanesulfonic acid, p-toluenesulfonic acid, oxalic acid, maleic acid, succinic acid benzoic acid and acetic acid, the most preferred acid is oxalic acid.

The acid salt of racemic condensed compound (5) is converted to free base of racemic condensed compound (6a+6b) by treating it with in organic or inorganic base in aqueous or organic or mixture of aqueous and water immiscible organic solvent. The organic base is selected from triethyl amine, diisopropylethyl amine, pyridine and the like while inorganic base is selected from hydroxides of alkali metals or alkaline earth metals such as sodium hydroxide, potassium hydroxide, lithium hydroxide; bicarbonates of alkali metals or alkaline earth metals such as sodium bicarbonate, potassium bicarbonate and the like; carbonates of alkali metals or alkaline earth metals such as sodium carbonate, potassium carbonate; and ammonia and mixtures thereof. The organic solvent is selected from aromatic hydrocarbon such as benzene, toluene, xylene; aliphatic esters such as ethyl acetate, propyl acetate, isopropyl acetate; ethers such as diisopropyl ether, tert.-butyl methyl ether; chlorinated hydrocarbons such as dichloromethane, ethylene dichloride, chloroform; lower aliphatic ketones such as acetone, methyl ethyl ketone, diethyl ketone; lower alcohols such as methanol, ethanol, propanol, isopropanol; acetonitrile or mixtures thereof. In a preferred reaction condition the oxalate salt (5, HA=oxalic acid) is converted to free base of racemic condensed compound (6a+6b) by treating it with aqueous ammonia in mixture of cyclohexane and water, followed by separating the organic layer, drying and concentration under reduced pressure.

In an another aspect of the present invention, there is provided a process for optical resolution of (R,S)—N,N-dimethyl-3-(2-thienyl)-3-(1-naphthalenyloxy)-propanamine (6a+6b) with DBTA (7, R=H) or DATA (7, R=OCH₃) to obtain crude (S)—N.N-dimethyl-3-(1-naphthyloxy)-3-(2-thienyl)propanamine dibenzoyl tartarate salt (8a) or (S)—N.N-dimethyl-3-(1-naphthyloxy)-3-(2-thienyl)propanamine di-p-anisoyl tartarate salt (9a) respectively. The solvents employed for the optical resolution is selected from aromatic hydrocarbon such as benzene, toluene, xylene; lower alcohols such as methanol, ethanol, propanol, isopropanol; lower aliphatic ketones such as acetone, methyl ethyl ketone, diethyl ketone; aliphatic esters such as ethyl acetate, propyl acetate, isopropyl acetate; ethers such as diisopropyl ether, tert.-butyl methyl ether; acetonitrile or mixtures thereof. The most preferred solvent for the resolution when DATA is used as resolving agent is toluene, ethyl acetate, isopropyl acetate, acetone or mixtures thereof. The most preferred solvent for the resolution when DBTA is used as resolving agent is ethyl acetate and methanol. The ratio of ethyl acetate:methanol in the solvent mixture is in the range from 99.9:0.1 to 0.1:99.9 (v/v), preferably 90:10 to 10:90 (v/v). Most preferred solvent ratio of ethyl acetate:methanol is 95:5 (v/v).

The comparative study of resolution of (R,S)—N,N-dimethyl-3-(2-thienyl)-3-(1-naphthalenyloxy)-propanamine (6a+6b) with DBTA in different solvents is depicted in the Table 1 below. The resolution was better in mixture of ethyl acetate:methanol is 95:5 (v/v).

TABLE 1

Study of resolution of (R,S)-N.N-dimethyl-3-(1-naphthyloxy)-3-(2-thienyl)propanamine (6a + 6b) by using DBTA in different solvents.

| Sr. No. | Solvent | Solvent ratio (v/v) | R-isomer content (%) | Yield (%) of DBTA salt (8a) |
|---|---|---|---|---|
| 1 | Ethyl acetate | — | 8.27 | 36.2 |
| 2 | Ethyl acetate | — | 8.90 | 37.0 |
| 3 | Isopropyl acetate:Methanol | 20:1 | 39.13 | 38.0 |
| 4 | Ethyl acetate:IPA | 19:1 | 7.07 | 37.6 |
| 5 | Ethyl acetate:Ethanol | 19:1 | 4.19 | 33.7 |
| 6 | Ethyl acetate:Acetone | 19:1 | 11.58 | 47.0 |
| 7 | Ethyl acetate:Methanol | 19:1 | 2.95 | 39.0 |

IPA = Isopropyl alcohol, v/v = volume by volume

The optical resolution is carried out with molar ratio of racemic condensed compound (6a+6b) to resolving agent DBTA or DATA is in the range 1:0.1 to 1:10, more preferably 1:0.5 to 1:1.2, most preferably 1:0.9 to 1:1.1.

The resolution is carried out at a temperature of 10-70° C., more preferably at 20-30° C. The resolution involve heating the reaction mixture up to reflux temperature of the solvent, more preferably to 50-60° C. and then allowing the solution to cool to room temperature and stirring for 5-20 hours, more preferably 8-15 hours.

Further aspect of the present invention is the purification of (S)-(+)-N,N-dimethyl-3-(2-thienyl)-3-(1-naphthalenyloxy)-propanamine dibenzoyl tartarate salt (8a) or (S)-(+)-N,N-dimethyl-3-(2-thienyl)-3-(1-naphthalenyloxy)-propanamine di-p-anisoyl tartarate salt (9a) by crystallization to obtain purity up to 99.8%. The crystallization is carried out from solvent selected from lower alcohols such as methanol, ethanol, isopropanol; lower aliphatic ketones such as acetone, methyl ethyl ketone, diethyl ketone; aliphatic esters such as ethyl acetate, propyl acetate, isopropyl acetate; ethers such as diisopropyl ether, tert.-butyl methyl ether; acetonitrile or mixtures thereof. The most preferred solvent for crystallization is mixture of methanol and ethyl acetate. The ratio of methanol to ethyl acetate is varied from 1:90 to 90:1, preferably 1:1 to 1:10. The ratio of substrate to solvent mixture is 1:1 to 1:30, preferably 1:5 to 1:15.

The crystallization is carried out by heating the reaction mixture to get clear solution, preferably up to reflux temperature of the solvent and then allowing the solution to cool to room temperature. The study of purification of (S)-(+)-N,N-dimethyl-3-(2-thienyl)-3-(1-naphthalenyloxy)-propanamine dibenzoyl tartarate salt (8a) by crystallization in different solvents is shown in Table 2.

Thus, the inventors of the present invention have surprisingly found that dibenzoyl-L-tartaric acid monohydrate is highly effective resolving agent for resolution of (R,S)—N,N-dimethyl-3-(2-thienyl)-3-(1-naphthalenyloxy)-propanamine (6a+6b). Moreover, use of DBTA provides following advantages that overcome the drawbacks of prior art.

1. The desired (S)-(+)-N,N-dimethyl-3-(2-thienyl)-3-(1-naphthalenyloxy)-propanamine (6a) isomer is obtained in better chiral purity up to 99.53%,
2. The desired (S)—N.N-dimethyl-3-(1-naphthyloxy)-3-(2-thienyl)propanamine (6a) isomer is obtained in comparable yield,
3. The present process avoids use of expensive solvents like tetrahydrofuran, and
4. The use of a cheaper resolving agent like DBTA makes the process highly cost effective.
5. Simple process, therefore easy to operate on large scale.

TABLE 2

Study of purification of (S)-(+)-N,N-dimethyl-3-(2-thienyl)-
3-(1-naphthalenyloxy)-propanamine dibenzoyl tartarate
salt (8a) by crystallization in different solvents.

| Sr. No. | R-isomer content (%) in crude 8a | Solvent | Solvent ratio (v/v) | R-isomer content (%) in pure 8a | Yield (%) |
| --- | --- | --- | --- | --- | --- |
| 1. | 2.95 | EA | — | 1.02 | 76 |
| 2. | 2.3 | Acetone | — | 1.05 | 68 |
| 3. | 2.3 | Ethanol | — | 0.48 | 72 |
| 4. | 5.5 | Ethanol | — | 1.05 | 74 |
| 5. | 5.5 | EA:Methanol | 10:1 | 0.81 | 74 |
| 6. | 2.34 | EA:Methanol | 10:1 | 0.42 | 72 |
| 7. | 5.5 | EA:Methanol | 8:1 | 0.18 | 50 |
| 8. | 5.5 | EA:Methanol | 16:1 | 0.91 | 70 |
| 9. | 2.34 | EA:Methanol | 16:1 | 0.42 | 72 |
| 10. | 4.95 | EA:Methanol | 16:1 | 0.93 | 74 |
| 11. | 4.95 | EA:Methanol | 16:1.5 | 0.27 | 60 |

EA = Ethyl acetate

In another embodiment, the present invention discloses a novel crystalline form of (S)—N.N-dimethyl-3-(1-naphthyloxy)-3-(2-thienyl)propanamine dibenzoyl-L-tartarate salt of formula 8a which is referred as Form I.

8a

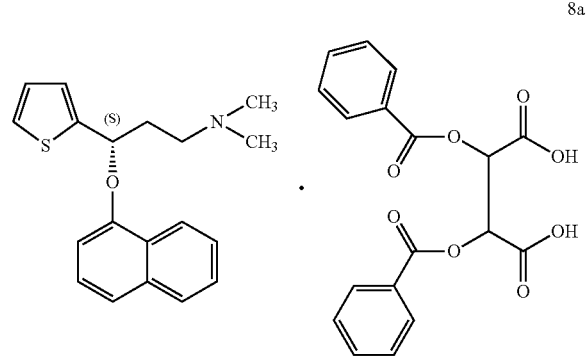

Figure 2:
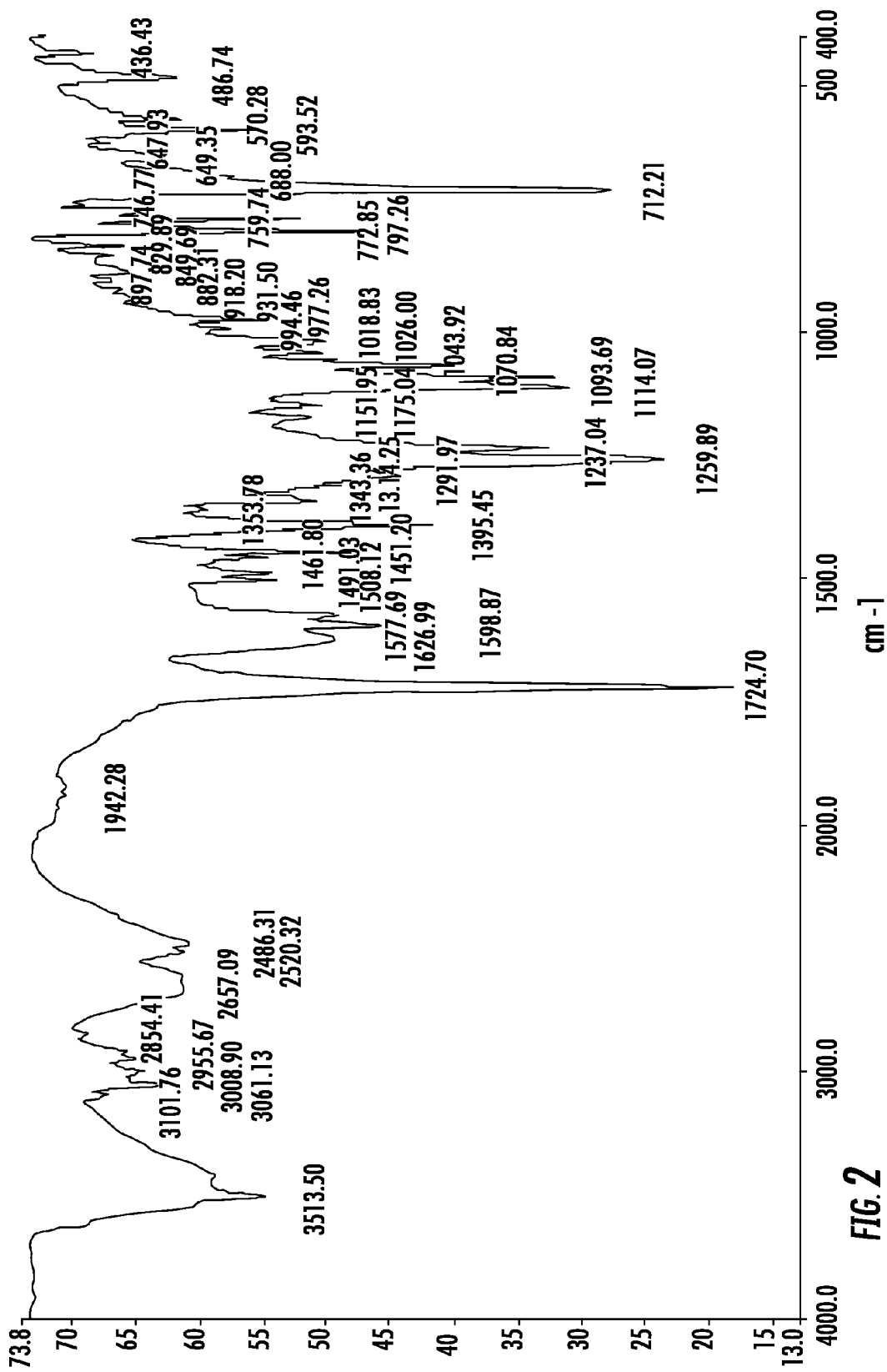
FIG. 2 Infra red spectrum of (S)—N,N-dimethyl-3-(1-napthlalenyloxy)-3-(2-thienyl) propanamine dibenzoyl L-tartarate salt (8a).
Figure 3:
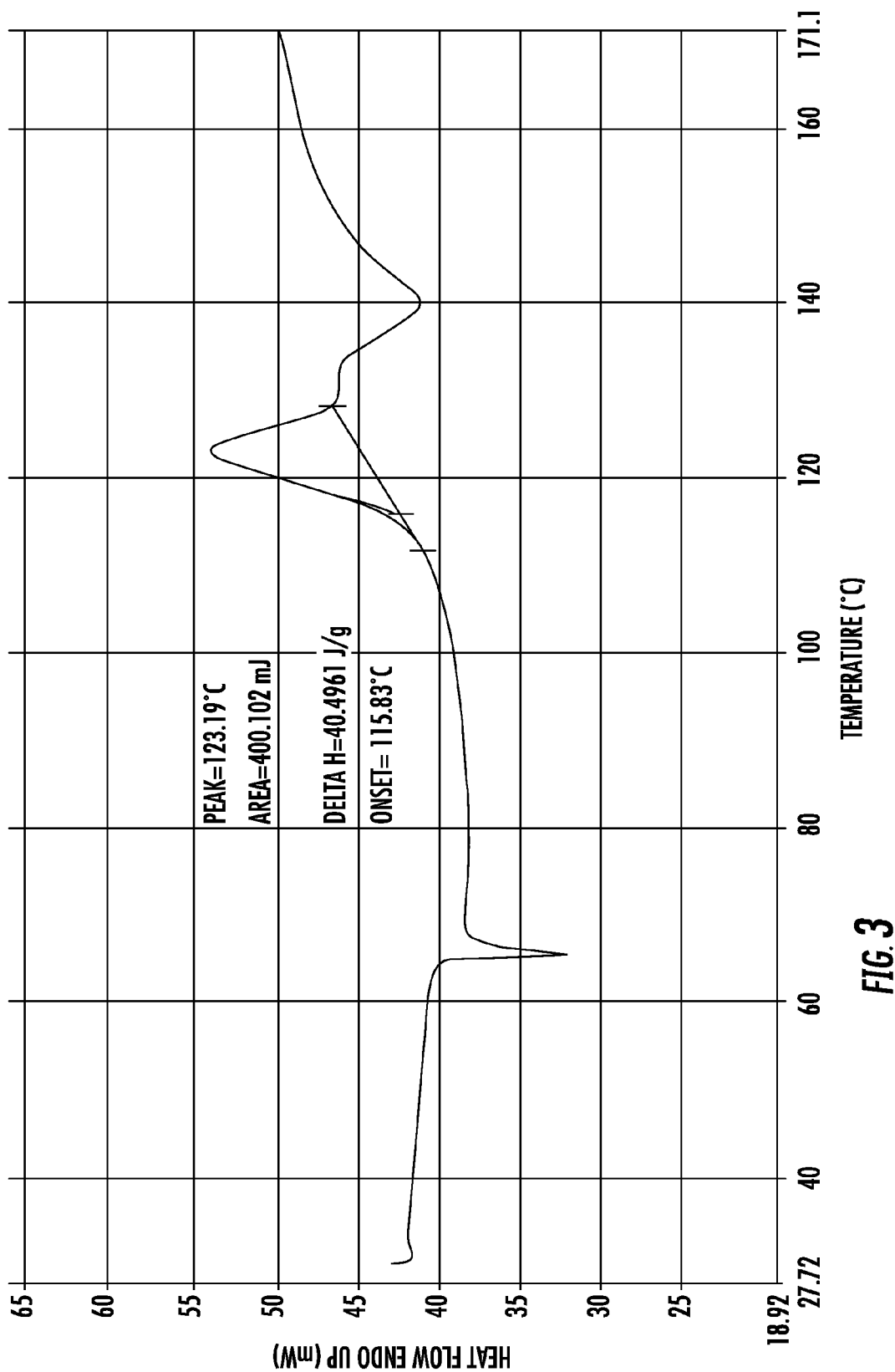
FIG. 3 Differential Scanning calorimetry of (S)—N,N-dimethyl-3-(1-napthlalenyloxy)-3-(2-thienyl) propanamine dibenzoyl L-tartarate salt (8a).

The Form I of crystalline (S)—N.N-dimethyl-3-(1-naphthyloxy)-3-(2-thienyl)propanamine dibenzoyl-L-tartarate salt (8a) of the present invention is characterized by the following data:

i) Powder X-ray diffraction pattern (PXRD): As represented in FIG. 1 that has significant reflections at 5.94, 7.29, 8.95 10.43, 11.64, 12.39, 13.42, 13.65, 14.99, 16.13, 16.96, 17.79, 17.96, 19.17, 20.08, 20.58, 20.95, 21.19, 21.39, 21.61, 22.00, 22.47, 22.73, 23.42, 24.38°, 24.93, 25.57, 25.84, 26.87, 27.10, 27.84, 28.76, 29.30, 30.00, 30.25, 31.27, 36.61±0.2 degrees two-theta;

ii) Infra red Spectrum: As depicted in FIG. 2 that has significant peaks at 3515, 3101.7, 2656.7, 2486.3, 1724.53, 1557.76, 1490.9, 1451.2, 1395.4, 1260.14, 1237.06, 1151.97, 1093.68, 1043.89, 797.19, 772.85, 712.27 cm$^{-1}$;

iii) Differential Scanning Calorimetry: As depicted in FIG. 3 which shows an endothermal maximum of melting at 123.19° C.;

iv) Melting point: At 118-120.5° C. and v) Moisture content (by KF): In the range 2.69-2.84%

In yet another embodiment, the present invention provides a novel salt (S)—N.N-dimethyl-3-(1-naphthyloxy)-3-(2-thienyl)propanamine di-p-anisoyl-L-tartarate of formula 9a 9a

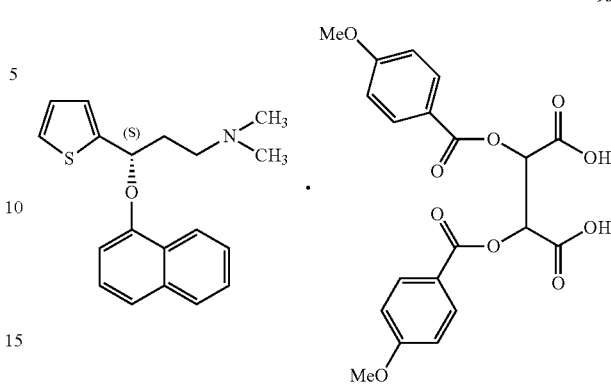

The (S)-(+)-N,N-dimethyl-3-(2-thienyl)-3-(1-naphthalenyloxy)-propanamine DBTA or DATA salt (8a or 9a) is treated with inorganic or inorganic base in aqueous or organic or mixture of aqueous and water immiscible organic solvent. The organic base is selected from triethyl amine, diisopropylethyl amine, pyridine and the like while inorganic base is selected from hydroxides of alkali metals or alkaline earth metals such as sodium hydroxide, potassium hydroxide, lithium hydroxide; bicarbonates of alkali metals or alkaline earth metals such as sodium bicarbonate, potassium bicarbonate and the like; carbonates of alkali metals or alkaline earth metals such as sodium carbonate, potassium carbonate; and ammonia and mixtures thereof. The organic solvent is selected from aromatic hydrocarbon such as benzene, toluene, xylene; aliphatic esters such as ethyl acetate, propyl acetate, isopropyl acetate; ethers such as diisopropyl ether, tert.-butyl methyl ether; chlorinated hydrocarbons such as dichloromethane, ethylene dichloride, chloroform; lower aliphatic ketones such as acetone, methyl ethyl ketone, diethyl ketone; lower alcohols such as methanol, ethanol, propanol, isopropanol; acetonitrile or mixtures thereof. In a preferred reaction condition the (S)-(+)-N,N-dimethyl-3-(2-thienyl)-3-(1-naphthalenyloxy)-propanamine DBTA or DATA salt (8a or 9a) is treated with aqueous ammonia in mixture of dichloromethane and water, followed by separating the organic layer, drying and concentration under reduced pressure to obtain enantiomerically pure (S)-(+)-N,N-dimethyl-3-(2-thienyl)-3-(1-naphthalenyloxy)-propanamine (6a) of chiral purity up to 99.8%.

The demethylation of (S)-(+)-N,N-dimethyl-3-(2-thienyl)-3-(1-naphthalenyloxy)-propanamine (6a) is achieved by treatment with phenyl chloroformate in presence of diisopropyl amine as base to obtain carbamate intermediate (10) in situ which is then subjected to hydrolysis with alkali such as sodium hydroxide or potassium hydroxide in polar aprotic solvent selected from dimethyl sulfoxide, sulfolane, dimethyl formamide, dimethyl acetamide, N-methylpyrrolidine-2-one, preferably in dimethyl sulfoxide to provide duloxetine base (11). The demethylation of racemic condensed product with phenyl chloroformate to carbamate intermediate and its subsequent alkaline hydrolysis is carried out according to procedure given in the product U.S. Pat. No. 5,023,269. Duloxetine free base (11) is an oily material which can be converted to oxalate salt by treating with oxalic acid in ethyl acetate to obtain duloxetine oxalate salt as solid compound.

In further embodiment, the present invention is characterized by the process for preparing duloxetine hydrochloride (1) that involves treatment of duloxetine base (11) with solution of 10-20% hydrochloric acid in lower alkanol such as methanol, ethanol, propanol, isopropanol preferably isopropanol; lower aliphatic ketones such as acetone, methyl ethyl ketone, diethyl ketone; aliphatic esters such as ethyl acetate, propyl acetate, isopropyl acetate; ethers such as diisopropyl ether, tert.-butyl methyl ether; acetonitrile or mixtures thereof. The most preferred solution of 10-20% hydrochloric acid is in isopropanol or ethyl acetate. The acidification is carried out solvent selected from lower alkanol such as methanol, ethanol, propanol, isopropanol preferably isopropanol; lower aliphatic ketones such as acetone, methyl ethyl ketone, diethyl ketone; aliphatic esters such as ethyl acetate, propyl acetate, isopropyl acetate; ethers such as diisopropyl ether, tert.-butyl methyl ether; acetonitrile or mixtures thereof, most preferably in isopropyl acetate or ethyl acetate. The acidification is carried out up to pH in the range 1-6, preferably in the range 2-3. The temperature during acidification is maintained in the range 0-50° C., preferably at 10-20° C.

Yet in another aspect, the present invention provides a process for purification of duloxetine hydrochloride by crystallization that comprises of:

i) adding crude duloxetine hydrochloride to a solvent selected from alcohols, such as methanol, ethanol, n-propanol, isopropanol; ketones, such as acetone, methyl ethyl ketone; esters, such as methyl acetate, ethyl acetate, ethyl formate, propyl acetate or a mixtures thereof, ii) heating the mixture to obtain clear solution, iii) cooling the solution, and iv) isolation of solid Preferred solvent for crystallization of duloxetine hydrochloride is a mixture of ethyl acetate and or acetone and methanol or ethyl acetate, acetone and methanol. The ratio of duloxetine hydrochloride to the solvent is in the range 2-10 times (weight by volume), preferably 4 to 7 times (weight by volume).

The heating is performed at temperature in the range 40° C. to reflux temperature of the mixture, most preferably at 50-60° C.

The ratio of duloxetine hydrochloride to the solvent is in the range 4 to 8 times weight by volume, preferably 5-7 times weight by volume.

The crystalline solid is isolated either by evaporation or by filtration.

Figure 4:
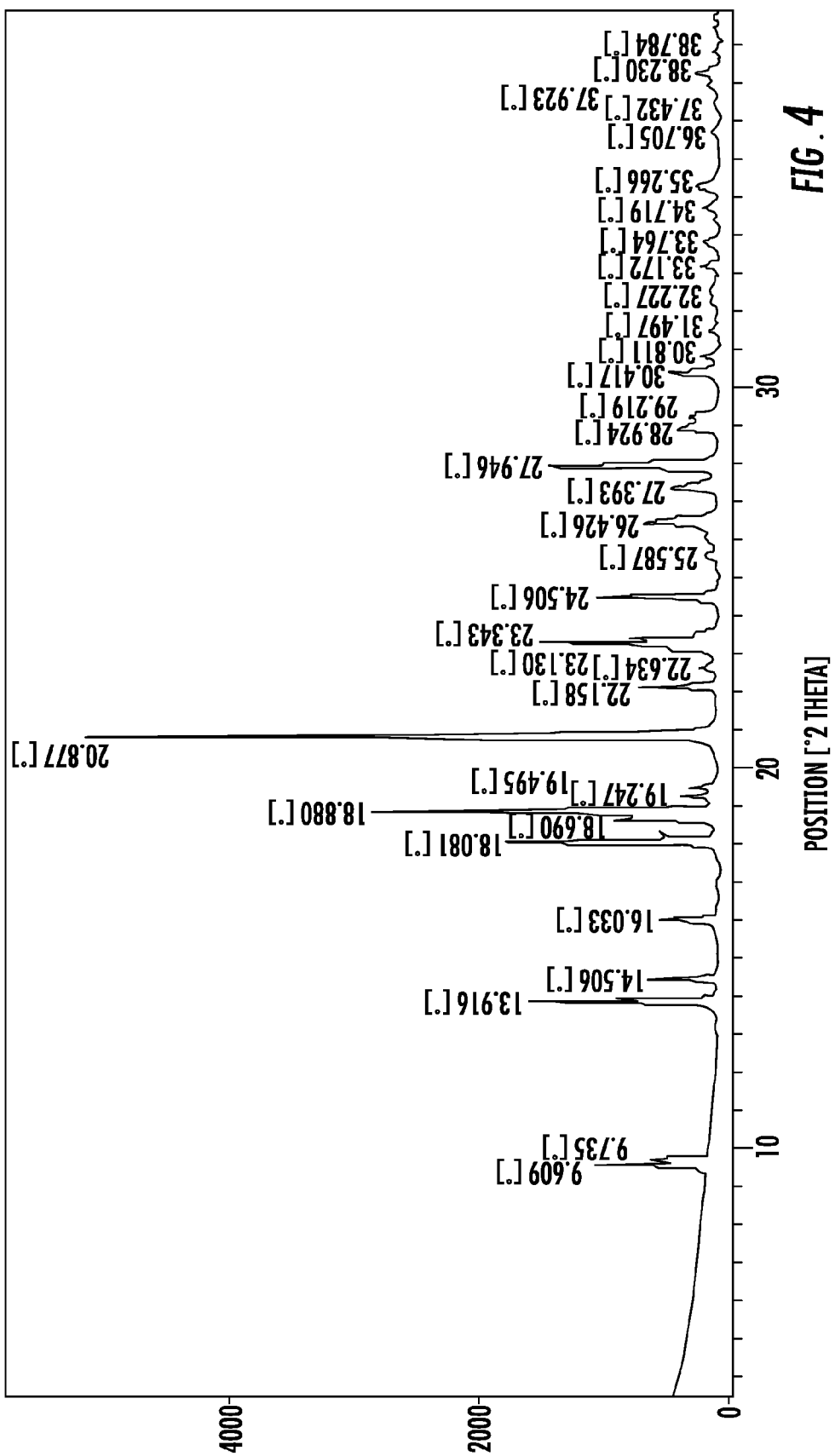
FIG. 4 Powder X-ray diffractogram of (S)—N,N-dimethyl-3-(1-napthlalenyloxy)-3-(2-thienyl) propanamine di-para-anisoyl L-tartarate salt (9a)."

In another aspect, the present invention provides crystalline Form A of duloxetine hydrochloride (1) characterized by PXRD as shown in FIG. 4. The PXRD of the crystalline duloxetine hydrochloride (1) obtained by the process of the present invention is similar to that of crystalline Form A described in patent application US 2006/0270859.

In an alternative embodiment, the present invention provides process for racemization of undesired isomer (R)-(−)-N,N-dimethyl-3-(1-naphthalenyloxy)-3-(2-thienyl)propanamine (6b) with KHMDS as base to obtain racemic compound (RS)—N,N-di methyl-3-(1-naphthyloxy)-3-(2-thienyl)propanamine free base (6a+6b) as shown in scheme III.

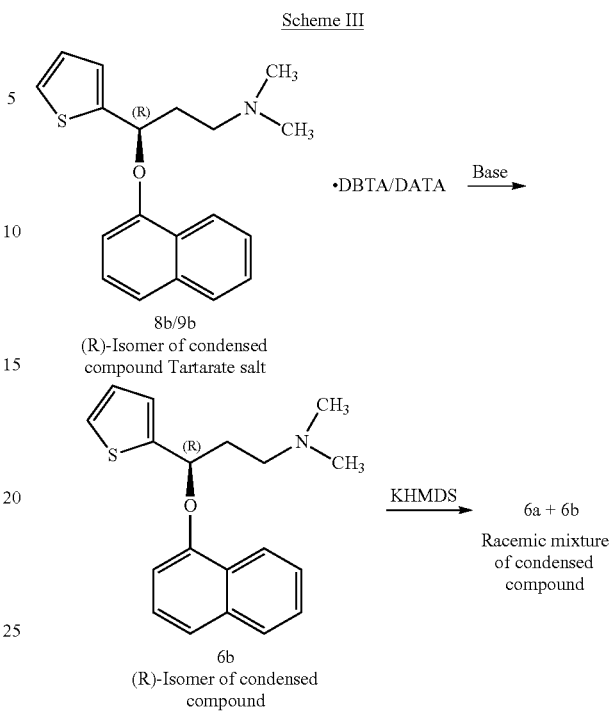

Scheme III

8b/9b
(R)-Isomer of condensed compound Tartarate salt 6b
(R)-Isomer of condensed compound 6a + 6b
Racemic mixture of condensed compound The racemization is carried out in organic solvent selected from aromatic hydrocarbons such as benzene, toluene, xylene, cyclic and acyclic ethers such as diethyl ether, diisopropyl ether, methyl tert. butyl ether, tetrahydrofuran, dioxane, esters such as ethyl acetate, isopropyl acetate, nitriles such as acetonitrile, propionitrile or mixtures thereof, most preferably toluene. The racemization is performed at temperature varying from 0-110° C., preferably at room temperature to 80° C., most preferably at 50-60° C. The racemic condensed compound (6a+6b) thus obtained is subjected to subsequent steps and converted to duloxetine hydrochloride (1) as described above.

The invention is further illustrated in the following representative examples and is not limit to the scope of the invention.

The room temperature refers to the temperature range of 25-30° C.

Example 1

Preparation of (±)-N,N-dimethyl-3-(1-naphthalenyloxy)-3-(2-thienyl)propanamine oxalate salt (5, HA=oxalic acid)

N,N-dimethyl-3-(2-thienyl)-3-hydroxypropanamine (2, racemic hydroxy compound) (50 gm) was dissolved in dimethyl sulfoxide (250 ml). To the clear solution sodamide (13.7 gm) was added at 20-25° C. in small lots within 10-15 minutes under nitrogen atmosphere. The resulting reaction mass was stirred for half an hour to get a clear solution. To this solution 1-fluoronaphthalene (3) (43.4 gm) was added in 20-25 minutes. The temperature was raised to 80-95° C. and stirred for 3-5 hours, then cooled to 25-30° C. Reaction mass added into cold-water (500 ml), pH was adjusted to 5.5-6.0 with acetic acid. Aqueous reaction mass washed with cyclohexane followed by pH adjustment between 10.5-11.0 with caustic solution. Reaction mixture was extracted with cyclohexane and organic layer concentrated under reduced pressure to provide thick oily mass of (±)-N,N-dimethyl-3-(1-naphthalenyloxy)-3-(2-thienyl)propanamine (4). The oily mass was dissolved in ethyl acetate (250 ml) and oxalic acid (30 gm) was added. Stirred at 50-60° C. for 1 hour then at 25-30° C. for 2 hours. Solid was filtered and dried to give racemic N,N-dimethyl-3-(1-naphthalenyloxy)-3-(2-thienyl)propanamine oxalate (5, HA=oxalic acid) as white solid. Yield: 75 gm.

Example 2

Preparation of (±)-N,N-dimethyl-3-(1-naphthalenyloxy)-3-(2-thienyl)propanamine oxalate salt (5, HA=oxalic acid)

Racemic hydroxy compound (2) (20 gm) was dissolved in N-methylpyrrolidinone (100 ml) to get clear solution. To this solution was added potassium bis(trimethylsilyl)amide (15% solution in toluene) (186.5 gm) slowly within 10-15 minutes. Stirred for half an hour then 1-fluoronaphthalene (3) (15.7 gm) was added in 20-25 minutes. Temperature was slowly raised to 80-90° C. and stirred further for 5-7 hours. Reaction mixture was cooled to 25-30° C. and then poured into cold-water (500 ml). The pH was adjusted to 5.5-6.0 with acetic acid. The aqueous layer was washed with toluene (100 ml). The pH of aqueous mass was adjusted to 10.5-11.0 with caustic solution then extracted with cyclohexane. The organic layer was concentrated under reduced pressure to give thick oily mass of (±)-N,N-dimethyl-3-(1-naphthalenyloxy)-3-(2-thienyl)propanamine (4). The oily mass was dissolved in ethyl acetate (100 ml). To this oxalic acid (12.15 gm) was added and stirred at 50-60° C. for 1 hour then at 25-30° C. for 2 hour. Solid was filtered, dried to give racemic N,N-dimethyl-3-(1-naphthalenyloxy)-3-(2-thienyl)propanamine oxalate (5, HA=oxalic acid) as off white solid. Yield: 28 gm.

Example 3

Preparation of (+)-N,N-dimethyl-3-(1-naphthalenyloxy)-3-(2-thienyl)propanamine di-p-anisoyl-(L)-tartarate salt (9a)

Racemic N,N-dimethyl-3-(1-naphthalenyloxy)-3-(2-thienyl)propanamine oxalate salt (5, HA=oxalic acid) (15 gm) was suspended in mixture of water (100 ml) and cyclohexane (50 ml). This suspension was basified with aqueous ammonia and then layers were separated. The cyclohexane layer was washed with water and concentrated under reduced pressure to give oily mass of (±)-N,N-dimethyl-3-(1-naphthalenyloxy)-3-(2-thienyl)propanamine free base (6a+6b). Yield: 10 gm.

Oily mass (10 gm) obtained above was dissolved in ethyl acetate (80 ml). Solution of di-p-anisoyl-(L)-tartaric acid (6.7 gm) in ethyl acetate (45 ml) was added in 10-15 minutes at 25-30° C. Temperature of mixture was slowly increased to 55-60° C. and then maintained under stirring for 15-20 minutes. Solution was cooled to 25-30° C. within 2 hours and then stirred for 8-10 hours. Solid was filtered, washed with 20 ml ethyl acetate and dried. Yield: 5.6 gm (off white solid) and chiral purity: 94.4%.

Example 4

Preparation of (S)-(+)-N,N-dimethyl-3-(1-naphthalenyloxy)-3-(2-thienyl)propanamine di-p-anisoyl-(L)-tartarate salt (9a)

Racemic N,N-dimethyl-3-(1-naphthalenyloxy)-3-(2-thienyl)propanamine free base (6a+6b) (10 gm) was dissolved in toluene or isopropyl acetate (120 ml). Solution of di-p-anisoyl-(L)-tartaric acid (6.7 gm) in acetone (15 ml) was added in 10-15 minutes at 25-30° C. Temperature was slowly increased to 50-55° C. and then maintained under stirring for 15-20 minutes. Reaction mixture cooled to room temperature in 2 hours and stirred for 10-12 hours. Solid was filtered, washed with ethyl acetate (20 ml) and dried. Yield: 4.8 gm (off white solid) and chiral purity: 94.2%.

Example 5

Preparation of pure (S)-(+)-N,N-dimethyl-3-(1-naphthalenyloxy)-3-(2-thienyl)propanamine di-p-anisoyl-(L)-tartarate salt (9a)

The tartarate salt (25 gm) obtained in example 4 was suspended in mixture of ethyl acetate (275 ml) and methanol (50 ml). Temperature of the mixture was raised to 60-65° C. to get a clear solution. The clear solution was then allowed to cool to room temperature and stirred for 1.5-2 hours. Solid was filtered, washed with ethyl acetate and dried. Yield: 18.8 gm and chiral purity: 99.8%.

Example 6

Preparation of (S)-(+)-N-methyl-3-(1-naphthalenyloxy)-3-(2-thienyl)propanamine (11, duloxetine free base)

The (S)—N,N-dimethyl-3-(1-naphthalenyloxy)-3-(2-thienyl)propanamine di-p-anisoyl-L-tartarate salt (9a) (100 gm) was added to biphasic solvent mixture of water (500 ml) and dichloromethane (250 ml). To the slurry aqueous ammonia was added to adjust the pH to 10.8 and stirred further for 15-30 minutes. Organic layer was separated, washed with water, brine and concentrated to get thick oily mass of (S)-(+)-N,N-dimethyl-3-(1-naphthalenyloxy)-3-(2-thienyl)propanamine (6a). Yield: 44 gm.

The above oily mass of 6a (44 gm) was added to toluene (220 ml). To the solution diisopropylethylamine (21.9 gm) was added and mixture was warmed to 45° C. To the mixture phenyl chloroformate (33.2 gm) was added dropwise and stirred for 2 hours at 55° C. Reaction mixture was cooled to room temperature and then basified with 2% NaHCO$_3$ solution (220 ml). Organic layer was separated, washed with water and concentrated to give oily mass of carbamate intermediate (10). The oily mass of carbamate intermediate was added to dimethyl sulfoxide (285 ml) followed by addition of solution of caustic lye (42.5 gm in 210 ml water). Reaction mixture was stirred for 3 hours at 90-92° C. Cooled to 15-20° C. and pH was adjusted between 5.5-6 with acetic acid. Aqueous layer was separated and washed with cyclohexane. The pH of aqueous mass was adjusted between 10.5-11 with acetic acid and then extracted with cyclohexane twice. Combined organic layer was washed with water and concentrated under reduced pressure to give duloxetine free base (11) as oily mass. Yield: 35 gm.

Example 7

Preparation of (S)—N.N-dimethyl-3-(1-naphthyloxy)-3-(2-thienyl)propanamine di-benzoyl-(L)-tartaric acid salt (8a)

(R,S)—N,N-dimethyl-3-(1-naphthalenyloxy)-3-(2-thienyl)propanamine oxalate salt (5, HA=oxalic acid) (255 gm) was suspended in a mixture of water (1275 ml) and cyclohexane (765 ml). This suspension was basified with aqueous ammonia solution (pH 12.5-13.5). Organic layer was separated, washed with water and concentrated under reduced pressure to give oily mass of racemic condensed compound, (R,S)—N.N-dimethyl-3-(1-naphthyloxy)-3-(2-thienyl)propanamine (6a+6b) (195 gm). The oily mass was dissolved in 2000 ml of mixture of methanol (5%) and ethyl acetate (95%). To this clear solution 1.0 mole equivalent of di-benzoyl-(L)-tartaric acid monohydrate (236.4 gm) was added. The clear solution was stirred for half an hour and seeded with crystals of (S)—N,N-dimethyl-3-(1-naphthylenyloxy)-3-(2-thienyl)propanamine dibenzoyl-(L)-tartarate salt (8a). The solution was stirred for 12-15 hours at 25-30° C. to get white thick slurry. The solid obtained was filtered, washed with ethanol (255 ml) and dried under reduced pressure.

Yield: 155 gm and chiral purity: 97.32%.

Example 8

Purification of (S)—N,N-dimethyl-3-(1-naphthyl-enyloxy)-3-(2-thienyl)propanamine dibenzoyl-L-tartaric acid salt (8a)

The (S)—N.N-dimethyl-3-(1-naphthyloxy)-3-(2-thienyl) propanamine di-benzoyl-(L)-tartaric acid salt (8a) (155 gm) obtained in example 7 was suspended in a mixture of ethyl acetate (775 ml) and methanol (77.5 ml) and the slurry so obtained was slowly warmed to 55-60° C. to get a clear solution. The solution was stirred for 15 minutes and allowed to cool down to room temperature slowly. The solution was stirred for 12-15 hours. The solid obtained was filtered, washed with ethyl acetate (2×127 ml) and dried under reduced pressure to get crystalline off white solid. Yield: 112.6 gm and chiral purity: 99.53%.

Example 9

Preparation of (S)—N-methyl-3-(1-naphthyleny-loxy)-3-(2-thienyl)propanamine (duloxetine free base) (11)

Pure (S)—N,N-dimethyl-3-(1-naphthalenyloxy)-3-(2-thienyl)propanamine dibenzoyl-L-tartaric acid salt (8a) (100 gm) obtained in example 8 was stirred in a mixture of water (500 ml) and cyclohexane (250 ml). Aqueous ammonia solution (100 ml) was charged to adjust the pH of slurry to 10.8 and the biphasic mass was stirred for 15-30 minutes. The organic layer was separated and aqueous layer was extracted with cyclohexane (250 ml). Organic layers were combined, washed with water and concentrated to get thick oily mass (S)—N,N-dimethyl-3-(1-naphthalenyloxy)-3-(2-thienyl) propanamine (6a). Yield: 45.0 gm. The oily mass obtained above was dissolved in toluene (225 ml) and diisopropylethylamine (23.18 gm) was added followed by phenyl chloroformate (35.10 gm) in drop wise manner. The solution was warmed to 55° C. and stirred for 2 hours. The reaction mass was cooled down, basified with 2% NaHCO$_3$ solution (225 ml) and organic layer was separated. Organic layer was washed with water and concentrated under reduced pressure to get oily mass of carbamate intermediate (10).

The oily mass of carbamate intermediate was dissolved in dimethyl sulfoxide (300 ml) to get clear solution followed by addition of NaOH solution (44.85 gm in 225 ml water). The mixture was stirred for 3 hours at 90° C. and then cooled to 15-20° C. The reaction mass was diluted with 2 liters of water and pH was adjusted between 5.5-6.0 with acetic acid followed by washing of aqueous mass with cyclohexane (2×200 ml). Combined organic layer was washed with water and concentrated under reduced pressure to get duloxetine free base (11) as oily mass. Yield: 38.0 gm.

Example 10

Preparation of (S)—N-methyl-3-(1-naphthyleny-loxy)-3-(2-thienyl)propanamine oxalic acid salt (du-loxetine oxalate salt)

Duloxetine free base (38 gm) was dissolved in ethyl acetate (650 ml) and 1 mole equiv of oxalic acid was added to the solution. The reaction mass was kept under stirring at 50-60° C. for 1 hour and then at room temperature for 2-3 hours. Solid obtained was filtered, washed with ethyl acetate and dried under reduced pressure to give duloxetine oxalate salt. Yield: 44 gm.

Example 11

Preparation of Duloxetine Hydrochloride Salt (1)

Duloxetine free base (35 gm) was dissolved in ethyl acetate (500 ml) and the resulting solution was cooled to 5-10° C. To this solution was added to ethyl acetate-HCl solution (about 12%) dropwise in 10-15 minutes. Slowly white solid started to precipitate out. Addition of ethyl acetate-HCl solution was continued till the pH of slurry reached between 2-3. The thick slurry mass was stirred at 15-20° C. for one hour. Solid was filtered, washed with ethyl acetate and dried under reduced pressure at 45-50° C. Yield: 35.3 gm, chemical purity: 99.8% (by HPLC) and chiral purity: 99.95% (by HPLC).

Example 12

Preparation of Duloxetine Hydrochloride Salt (1)

Duloxetine free base (10 gm) was dissolved in isopropyl acetate (100 ml) and cooled to 5-10° C. To this solution isopropyl alcohol-HCl solution (about 15%) was added dropwise till pH was between 2-3. The resulting thick slurry stirred at 15-20° C. for two hours. Solid was filtered, washed with isopropyl acetate (20 ml), dried under reduced pressure at 45-50° C. Yield: 8.2 gm; chemical purity: 99.8% (by HPLC) and chiral purity: 99.95%.

Example 13

Purification of Duloxetine Hydrochloride (1)

Duloxetine hydrochloride (115 gm) was suspended in mixture of cyclohexane (350 ml) and water (575 ml). The biphasic mass was treated with aqueous ammonia (pH 12.5-13.0). Organic layer was separated, washed with water and concentrated under reduced pressure to afford the oily mass (100 gm). This oily mass was dissolved in ethyl acetate (1800 ml) and solution was cooled to 5-10° C. A solution of HCl in ethyl acetate (10-15% strength) was added till the pH is 5.5-6.0. The thick slurry was maintained under stirring. Solid obtained was filtered, washed with ethyl acetate (150 ml) and dried under reduced pressure to obtain pure duloxetine hydrochloride as white solid. Yield: 100 gm and chiral purity: 99.93%

Example 14

Purification of Duloxetine Hydrochloride (1) by Crystallization from Mixture of Ethyl Acetate and Methanol

Duloxetine hydrochloride (100 gm) was suspended in mixture of ethyl acetate (600 ml) and methanol (50 ml). The mixture was heated to 60-65° C. and stirred for 1 hour. The slurry was then cooled to room temperature and stirred for 2 hours. The solid obtained was filtered, washed with ethyl acetate (2×100 ml) and dried under reduced pressure for 10-12 hours. Pure duloxetine hydrochloride was obtained as off white colored solid. Yield: 90 gm

Example 15

Purification of Duloxetine Hydrochloride (1) by Crystallization from Mixture of Acetone and Methanol

Duloxetine hydrochloride (50 gm) was added to mixture of acetone (200 ml) and methanol (25 ml) at 25-35° C. The slurry was heated to 55-60° C. and stirred for 30 minutes. Cooled to 25-35° C., stirred for 15-20 minutes and again cooled to 5-10° C. and stirred for 2 hours. Solid was filtered, washed with acetone (50 ml), ethyl acetate (2×100 ml) and dried under reduced pressure at 45° C. for 10 hours to get 43 g of white to off white solid having purity 99.92% by HPLC.

Example 16

Purification of Duloxetine Hydrochloride (1) by Crystallization from Mixture of Acetone, Ethyl Acetate and Methanol

Duloxetine hydrochloride (50 gm) was added to mixture of acetone (200 ml), ethyl acetate (100 ml) and methanol (25 ml) at 25-35° C. The slurry was heated to 55-60° C. and stirred for 30 minutes. Cooled to 25-35° C. stirred for 15-20 minutes and again cooled to 5-10° C. and stirred for 2 hours. Solid was filtered, washed with acetone (50 ml), ethyl acetate (2×100 ml) and dried under reduced pressure at 45° C. for 10 hours to get white to off white solid. Yield: 43 gm and purity 99.92% by HPLC.

Example 17

Purification of Duloxetine Hydrochloride (1) by Crystallization from Mixture of Acetone, Ethyl Acetate and Methanol

Duloxetine hydrochloride (50 gm) was added to mixture of ethyl acetate (300 ml), methanol (25 ml) and acetone (25 ml) at 25-35° C. The slurry was heated to 55-60° C. and stirred for 30 minutes. Cooled to 25-35° C. stirred for 15-20 minutes and again cooled to 5-10° C. and stirred for 2 hours. Solid was filtered, washed with acetone (50 ml), ethyl acetate (2×100 ml) and dried under reduced pressure at 45° C. for 10 hours to get white to off white solid. Yield: 45 gm and purity 99.9% by HPLC.

Example 18

Process for racemization of (R)-(−)-N,N-dimethyl-3-(1-naphthalenyloxy)-3-(2-thienyl)propanamine (6b) to obtain racemic (RS)—N,N-dimethyl-3-(1-naphthalenyloxy)-3-(2-thienyl)propanamine (6a+6b)

The ethyl acetate solution (mother liquor from resolution step, examples 3 and 4) that is enriched with R isomer, (R)-(−)-N,N-dimethyl-3-(1-naphthalenyloxy)-3-(2-thienyl) propanamine (6b) was concentrated under reduced pressure to obtain thick oily mass. Thick oily mass was dissolved in toluene (120 ml). To the solution water (60 ml) was added and pH of biphasic system was adjusted to 10.0-10.5 with caustic lye solution. Toluene layer was separated, washed with water and concentrated to afford oily residue (30 gm). The oily residue was again dissolved in toluene (150 ml) having moisture content less than 0.2% and to this solution dimethyl sulfoxide (75 ml) was added. To this mixture solution of potassium bis(trimethylsilyl)amide (15% solution in toluene) (63.8 gm) was added. Temperature was slowly raised to 50-60° C. and maintained under stirring for 4-6 hours. Reaction mass was cooled to room temperature and water (250 ml) was added. Stirred for 15 minutes and separated the organic layer. Organic layer was washed with water and concentrated under reduced pressure to get racemic condensed compound, (R,S)—N,N-dimethyl-3-(1-naphthalenyloxy)-3-(2-thienyl) propanamine (6a+6b) as an oily mass. Yield: 30 gm.

The invention claimed is:

1. A novel process for synthesis of duloxetine hydrochloride of formula (1),

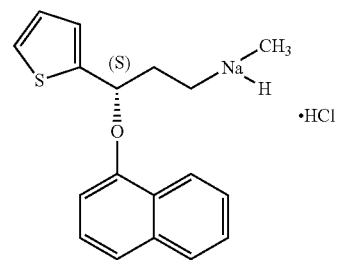

the process comprising the steps of:
i) reaction of (RS)—N.N-di methyl-3-hydroxy-3-(2-thienyl)propanamine (2, racemic hydroxy compound) of formula (2),

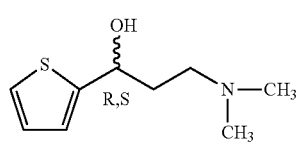

with 1-fluoronaphthalene of formula (3),

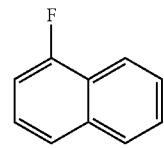

in aprotic polar organic solvent in presence of a base selected from sodamide, potassium amide, potassium bis(trimethylsilyl)amide to obtain (RS)—N.N-di methyl-3-(1-naphthyloxy)-3-(2-thienyl)propanamine (racemic condensed compound) of formula 4,

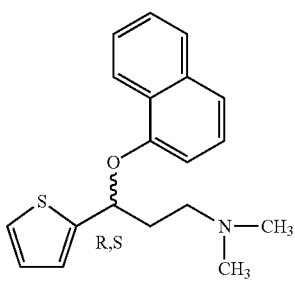

4 ii) optionally isolation of racemic condensed compound as acid addition salt of organic or inorganic acid of formula (5),

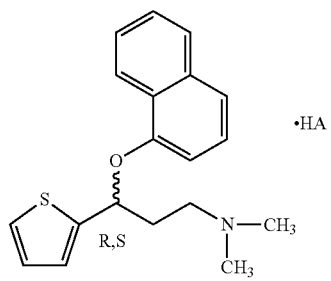

5 where HA is organic or inorganic acid, iii) conversion of acid salt (5) to free base (R,S)—N.N-di methyl-3-(1-naphthyloxy)-3-(2-thienyl)propanamine of formula (6a+6b),

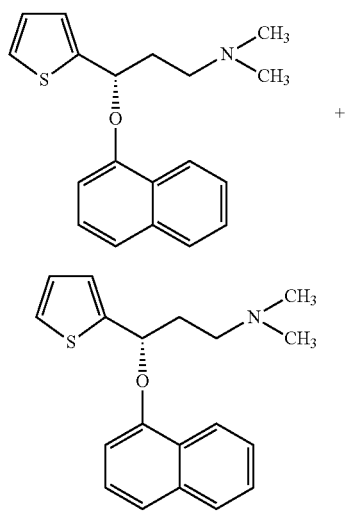

6a

+

6b by treatment with organic or inorganic base in aqueous or organic or mixture of aqueous and water immiscible organic solvent, iv) optical resolution of racemic condensed compound free base (6a+6b) with dibenzoyl-L-tartaric acid (DBTA) of formula (7) wherein R=H, or di-p-anisoyl-L-tartaric acid (DATA) of formula (7) wherein R=OCH$_3$,

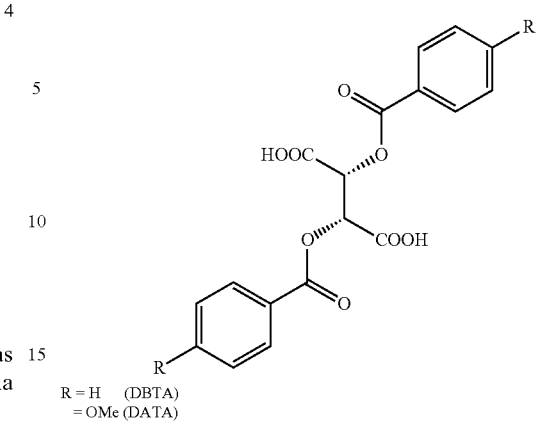

7

R = H (DBTA)
= OMe (DATA)

is carried out in organic solvent selected from aromatic hydrocarbons; lower alcohols; lower aliphatic ketones; aliphatic esters; ethers; acetonitrile, or mixtures thereof to get crude corresponding (S)-isomer tartarate salt of formula (8a or 9a),

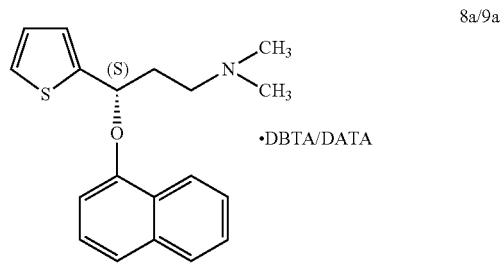

8a/9a respectively, v) optionally purification of (S)-isomer tartarate salt (8a or 9a) by crystallization from a suitable organic solvent or mixture of two or more solvents, vi) conversion of (S)-isomer tartarate salt (8a or 9a) to free base (S)—N.N-di methyl-3-(1-naphthyloxy)-3-(2-thienyl)propanamine of formula (6a),

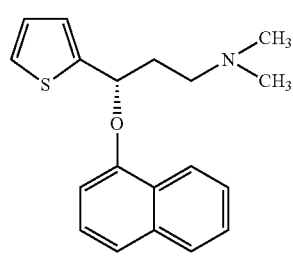

6a by treatment with organic or inorganic base in aqueous or organic or mixture of aqueous and water immiscible organic solvent, vii) demethylation of free base (6a) by treatment with phenyl chloroformate in presence of diisopropylethyl amine in toluene to get carbamate intermediate of formula (10),

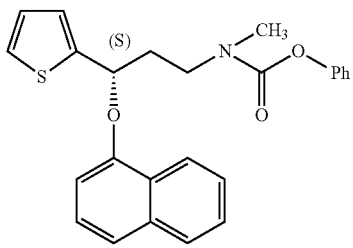

viii) hydrolysis of carbamate intermediate (10) with sodium hydroxide in polar aprotic solvent to give duloxetine base of formula (11),

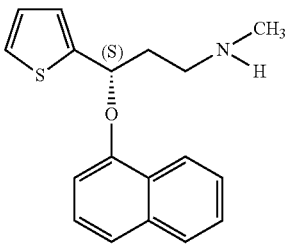

ix) conversion of duloxetine base (11) to duloxetine hydrochloride (1) in an organic solvent or mixture of organic solvents, and x) optionally purification of duloxetine hydrochloride (1) by crystallization.

2. The process according to claim 1, wherein the aprotic solvent used in step i) is selected from dimethyl sulfoxide, sulfolane, dimethyl formamide, dimethyl acetamide and N-methylpyrrolidine-2-one.

3. The process according to claim 1, wherein the reaction is carried out at a temperature of room temperature to 150° C.

4. The process according to claim 1, wherein the base used in step i) of the reaction is sodamide.

5. The process according to claim 1, wherein the reaction is carried out with a molar ratio of racemic hydroxy compound (2) to base in the range from 1:1 to 1:5.

6. The process according to claim 1, wherein the (RS)—N.N-di methyl-3-(1-naphthyloxy)-3-(2-thienyl)propanamine (racemic condensed compound) of formula (4),

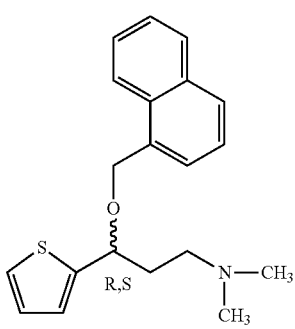

is isolated as acid addition salt of formula (5),

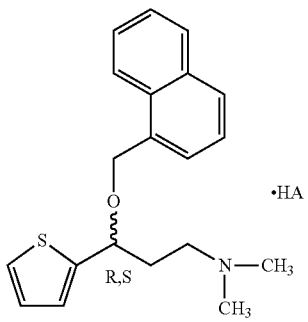

wherein HA is hydrochloric acid, sulfuric acid, phosphoric acid, methanesulfonic acid, p-toluenesulfonic acid, oxalic acid, maleic acid, succinic acid benzoic acid or acetic acid.

7. The process according to claim 1, wherein step iii) is carried out by treating the acid salt of formula (5),

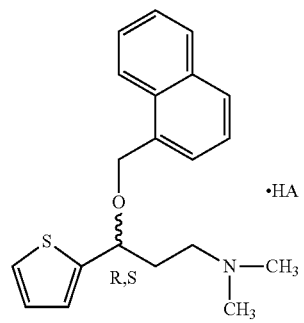

wherein HA is organic or inorganic acid, with a base in a mixture of organic solvent and water.

8. The process according to claim 1, wherein the solvent employed in step iv) for optical resolution is selected from benzene, toluene, xylene, methanol, ethanol, isopropanol, acetone, methyl ethyl ketone, diethyl ketone, ethyl acetate, propyl acetate, isopropyl acetate, diisopropyl ether, tert.-butyl methyl ether; acetonitrile or mixtures thereof.

9. The process according to claim 8, wherein the solvent used for the optical resolution when di-p-anisoyl-L-tataric acid (DATA) of formula (7),

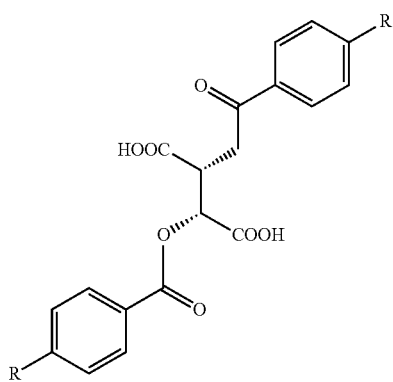

wherein R=OMe is used as resolving agent, is selected from toluene, ethyl acetate, isopropyl acetate, acetone or mixtures thereof.

10. The process according to claim 8, wherein the solvent used for the optical resolution when dibenzoyl-L-tartaric acid (DBTA) of formula 7,

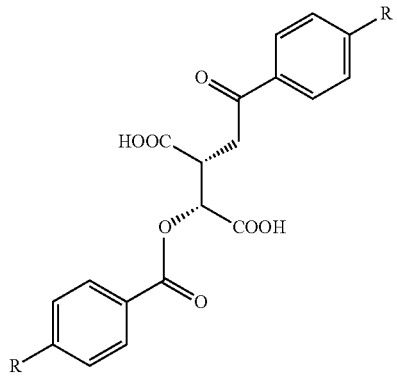

wherein R=H is used as resolving agent, is ethyl acetate and methanol.

11. The process according to claim 10, wherein the ratio of ethyl acetate:methanol in the solvent mixture is 95:5 (v/v).

12. The process according to claim 9, wherein the optical resolution is carried out with molar ratio of racemic condensed compound of formula (6a+6b),

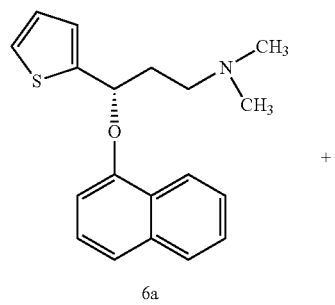

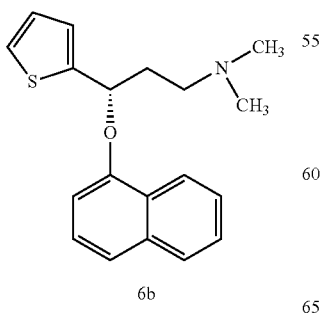

to resolving agent dibenzoyl-L-tartaric acid (DBTA) of formula (7),

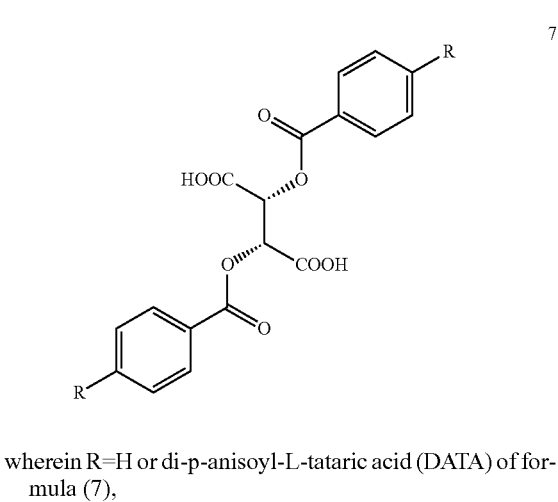

wherein R=H or di-p-anisoyl-L-tataric acid (DATA) of formula (7),

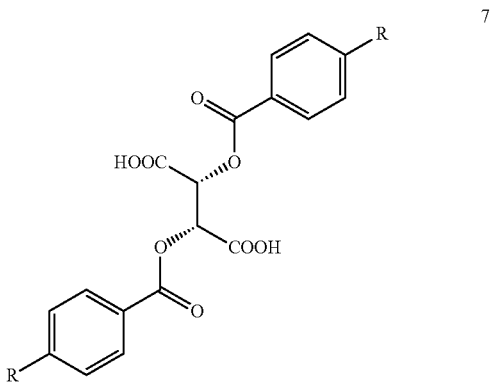

wherein R=OMe is in the range of 1:0.5 to 1:1.2.

13. The process according to claim 9, wherein the optical resolution is carried out at a temperature of 10-70° C.

14. The process according to claim 1, wherein step v) of optional purification of tartarate salt of (S)-isomer of formula (8a) or of formula (9a),

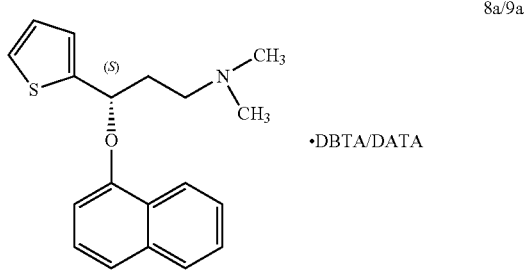

by crystallization is carried out from solvent selected from lower alcohols, lower aliphatic ketones, aliphatic esters, ethers, acetonitrile or mixtures thereof.

15. The process according to claim 14, wherein the solvent is a mixture of methanol and ethyl acetate in the ratio of 1:1 to 1:10 (volume/volume).

16. The process according to claim 15, wherein the crystallization is carried out with the ratio of substrate to solvent in the range of 1:1 to 1:30, (weight by volume).

17. The process according to claim 16, wherein the crystallization is carried out by heating the reaction mixture to get a clear solution, and then allowing the solution to cool to room temperature.

18. The process according to claim 1, wherein step vi) is carried out by treating the tartarate salt of formula (8a) or (9a),

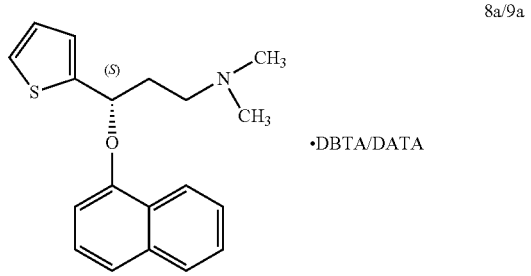

8a/9a

·DBTA/DATA with a base in a mixture of organic solvent such as dichloromethane and water.

19. The process according to claim 1, wherein step vii) is carried out by treatment of (S)-isomer of condensed compound of formula (6a),

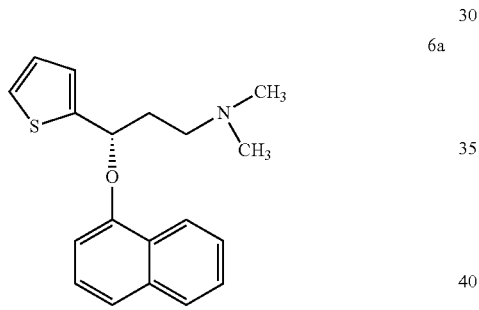

6a with phenyl chloroformate in presence of diisopropyl amine base in toluene as solvent.

20. The process according to claim 1, wherein step viii) is carried out with sodium hydroxide in polar aprotic solvent selected from dimethyl sulfoxide, sulfolane, dimethyl formamide, dimethyl acetamide, or N-methylpyrrolidine-2-one.

21. The process according to claim 1, wherein step ix) is carried out with a solution of 10-20% hydrochloric acid in an organic solvent.

22. The process according to claim 21, wherein the solvent is selected from lower aliphatic ketones, aliphatic esters, ethers, acetonitrile or mixtures thereof.

23. The process according to claim 22, wherein the reaction is carried out at pH in the range of 1-6.

24. The process according to claim 23, wherein the reaction is carried out at 0-50° C.

25. The process according to claim 1, wherein the step x) of purification of duloxetine hydrochloride by crystallization comprises of:
i) adding crude duloxetine hydrochloride to a solvent selected from alcohols, ketones, esters or mixtures thereof,
ii) heating the mixture to obtain a clear solution,
iii) cooling the solution, and
iv) isolation of crystallized solid duloxetine hydrochloride.

26. The process according to claim 25, wherein the solvent used for crystallization of duloxetine hydrochloride is a mixture of ethyl acetate and methanol, or acetone and methanol, or ethyl acetate, acetone and methanol.

27. The process according to claim 26 wherein the ratio of duloxetine hydrochloride to the solvent is in the range of 2-10 times (weight by volume).

28. The process according to claim 27, wherein the heating is performed at temperature in the range of 40° C. to reflux temperature of the mixture.

29. The process according to claim 28, wherein the crystalline solid is isolated either by evaporation or by filtration.

30. A process for optical resolution of racemic condensed compound free base of formula (6a+6b),

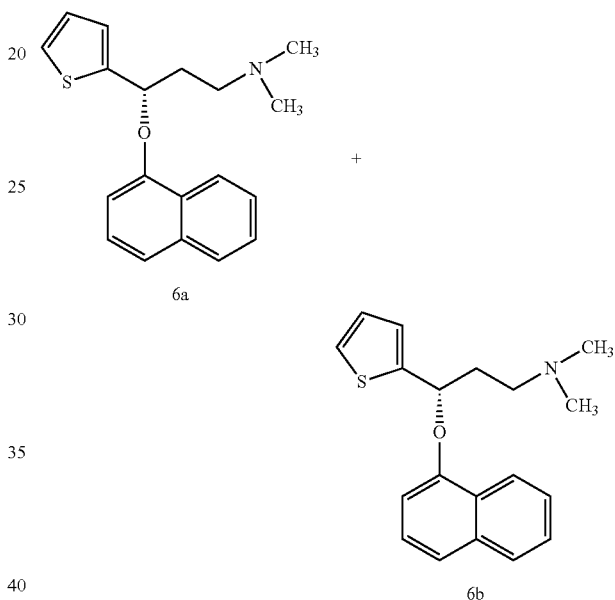

with dibenzoyl-L-tartaric acid (DBTA) or di-p-anisoyl-L-tartaric acid (DATA) of formula (7) wherein R=H or di-p-anisoyl-L-tartaric acid (DATA) of formula (7) wherein R=OCH₃,

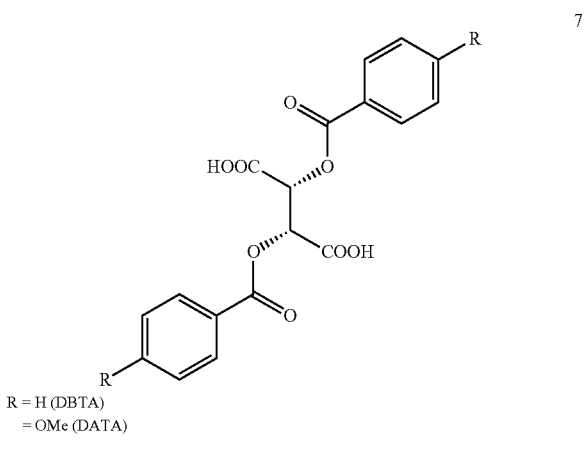

R = H (DBTA)
= OMe (DATA)

in organic solvent to get crude corresponding (S)-isomer tartarate salt of formula (8a) or (9a),

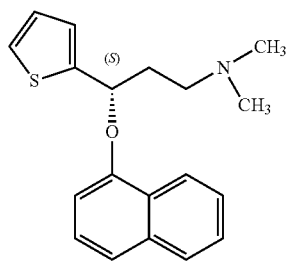

·DBTA/DATA

8a/9a respectively.

31. The process according to claim 30, wherein the solvent is selected from aromatic hydrocarbons, lower alcohols, lower aliphatic ketones, aliphatic esters, ethers, acetonitrile or mixtures thereof.

32. The process according to claim 31, wherein the solvent for the resolution when dibenzoyl-L-tartaric acid (DBTA) of formula 7,

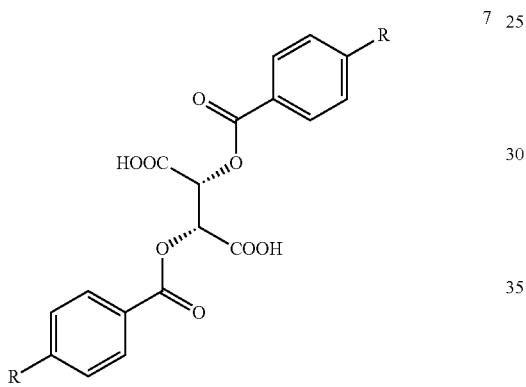

7 wherein R=OMe is used as resolving agent is selected from toluene, ethyl acetate, isopropyl acetate, acetone or mixtures thereof.

33. The process according to claim 31, wherein the solvent for the resolution when dibenzoyl-L-tartaric acid (DBTA) of formula 7,

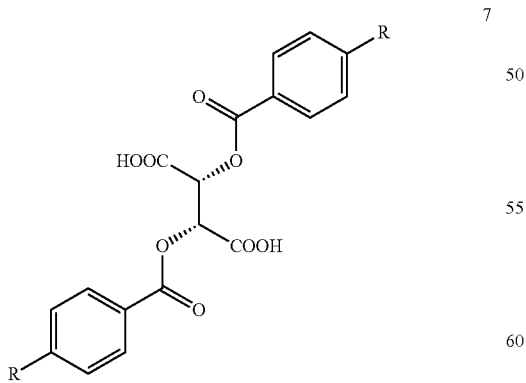

7 wherein R=H is used as resolving agent is a mixture of ethyl acetate and methanol.

34. The process according to claim 33, wherein the ratio of ethyl acetate:methanol in the solvent mixture is 95:5 (v/v).

35. The process according to claim 32, wherein the optical resolution is carried out with molar ratio of racemic condensed compound of formula (6a+6b),

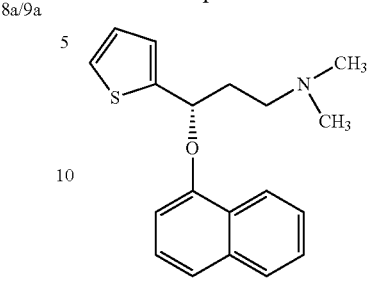

6a

+

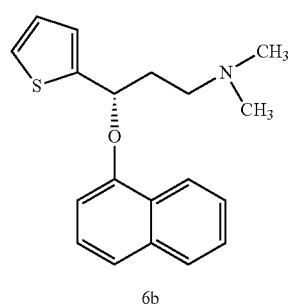

6b to resolving agent dibenzoyl-L-tartaric acid (DBTA) of formula (7),

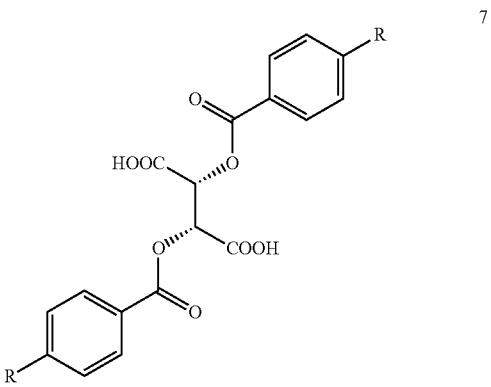

7 wherein R=H or di-p-anisoyl-1-tartaric acid (DATA) of formula (7),

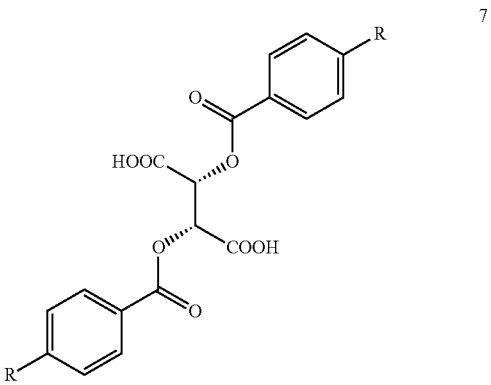

7 wherein R=OMe is in the range 1:0.1 to 1:10.

36. The process according to claim 35, wherein the optical resolution is carried out at a temperature of 10-70° C.

37. A process for purification of (S)-isomer tartarate salt of formula (8a) or of formula (9a),

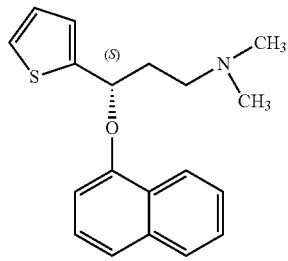

·DBTA/DATA

8a/9a by crystallization from a suitable organic solvent or mixture of two or more solvents selected from lower alcohols, lower aliphatic ketones, aliphatic esters, ethers, acetonitrile or mixtures thereof.

38. The process according to claim 37, for purification of (S)-isomer tartarate salt wherein the crystallization is carried out from a mixture of methanol and ethyl acetate.

39. The process according to claim 38, wherein the ratio of methanol to ethyl acetate is 1:1 to 1:10 (volume/volume).

40. The process according to claim 39, wherein the crystallization is carried out with the ratio of substrate to solvent in the range from 1:1 to 1:30 (weight by volume).

41. The process according to claim 40, wherein the crystallization is carried out by heating the reaction mixture to get a clear solution, and then allowing the solution to cool to room temperature.

42. A process for racemization of undesired isomer (R)-(−)-N,N-dimethyl-3-(1-naphthalenyloxy)-3-(2-thienyl)propanamine [(R)-isomer of condensed compound] of formula (8a) or of formula (9a),

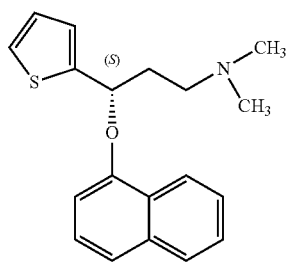

·DBTA/DATA

8a/9a with potassium bis(trimethylsilyl)amide as base to obtain racemic compound (R,S)—N,N-di methyl-3-(1-naphthyloxy)-3-(2-thienyl)propanamine free base (6a+6b),

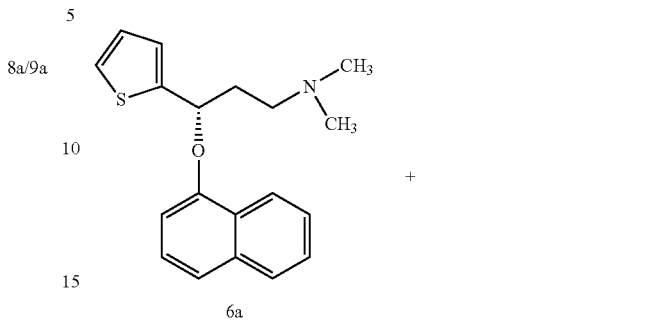

6a

+

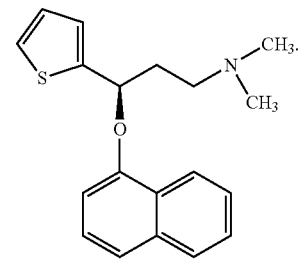

43. The process according to claim 42, wherein the racemization is carried out in an organic solvent selected from aromatic hydrocarbons, acyclic ethers, esters, nitriles or mixtures thereof.

44. The process according to claim 43, wherein the racemization is performed at temperature varying from 0-110° C.

45. The process according to claim 43, wherein the racemization is carried out in an organic solvent selected from benzene, toluene, xylene, cyclic- and diisopropyl ether, methyl tert, butyl ether, tetrahydrofuran, dioxane, ethyl acetate, isopropyl acetate, acetonitrile, propionitrile, dimethyl sulfoxide, sulfolane or mixtures thereof.

46. The process according to claim 43, wherein the racemization is carried out in an organic solvent mixture of toluene and dimethyl sulfoxide.

47. The process according to claim 43, wherein the racemization is performed at temperature of 50-60° C.

* * * * *